United States Patent
Genet et al.

(10) Patent No.: US 6,464,731 B1
(45) Date of Patent: Oct. 15, 2002

(54) CATIONIC MONOBENZENE NITROPHENYLENEDIAMINES, THEIR USE IN DYEING KERATINOUS FIBERS, DYEING COMPOSITIONS COMPRISING THEM AND DYEING PROCESSES

(75) Inventors: Alain Genet, Aulnay Sous Bois; Alain Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/479,079

(22) Filed: Jan. 7, 2000

(30) Foreign Application Priority Data

Jan. 8, 1999 (FR) .......................... 99 00150

(51) Int. Cl.⁷ .................................. A61K 7/13
(52) U.S. Cl. .................. 8/405; 8/406; 8/409; 8/410; 546/184; 548/400
(58) Field of Search .................. 8/405, 406, 409, 8/410; 546/184; 448/400

(56) References Cited

U.S. PATENT DOCUMENTS

| | | | |
|---|---|---|---|
| 3,817,698 A | 6/1974 | Kalopissis et al. | 8/10.1 |
| 4,018,556 A | 4/1977 | Kalopissis et al. | 8/10.1 |
| 4,888,025 A | 12/1989 | Bugaut et al. | 8/405 |
| 5,135,543 A | 8/1992 | Chan et al. | 8/405 |
| 5,139,532 A | 8/1992 | Chan et al. | 8/405 |
| 5,256,823 A | 10/1993 | Chan et al. | 564/284 |
| 5,735,910 A | 4/1998 | Lagrange et al. | 8/415 |
| 5,874,618 A | 2/1999 | Lagrange et al. | 564/305 |

FOREIGN PATENT DOCUMENTS

| | | |
|---|---|---|
| BE | 616 439 | 10/1965 |
| DE | 198 02 940 | 8/1999 |
| EP | 0 673 926 | 9/1995 |
| FR | 1 221 122 | 5/1960 |
| FR | 1 565 247 | 4/1969 |
| FR | 2 520 358 | 7/1983 |
| GB | 909 700 | 10/1962 |
| GB | 1 164 824 | 9/1969 |
| GB | 1164824 | * 9/1969 |
| GB | 1 199 641 | 7/1970 |
| LU | 54 049 | 3/1969 |
| WO | WO 99/03836 | 1/1999 |

OTHER PUBLICATIONS

Ermitas Alcalde et al. (Heterocyclic Betaines. Novel Ethyleneimidazolium Benzimidazolate Inner Salts. Synthesis, Characterization, and Transformation into 2-Vinyl-1 H-benzimidazoles). Chem. Lett. (12), 2357-60, (1992).*

Chemical Abstracts, vol. 72, No. 2, Jan. 12, 1979, Abtract No. 4329y (JP 06 910910).

English language Derwent Abstract of DE 198 02 940. Aug. 5, 1999.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, LLP

(57) ABSTRACT

The subject of the invention is cationic monobenzene nitrophenylenediamines having at least one cationic charge delocalized over an unsaturated 5-membered polynitrogenous heterocycle, to their use as direct dye in dyeing compositions for keratinous substances, in particular for human keratinous fibers, such as the hair, to the dyeing compositions comprising them and to the dyeing processes employing these compositions.

23 Claims, No Drawings

CATIONIC MONOBENZENE NITROPHENYLENEDIAMINES, THEIR USE IN DYEING KERATINOUS FIBERS, DYEING COMPOSITIONS COMPRISING THEM AND DYEING PROCESSES

The present invention relates to monobenzene nitrophenylenediamines having at least one cationic charge delocalized on an unsaturated 5-membered polynitrogenous heterocycle, and comprising at least one cationic group which is chosen from certain aliphatic chains, to their use as direct dyes in dyeing applications for keratinous substances, in particular for human keratinous fibers and especially the hair, to the dyeing compositions comprising them, and to the dyeing processes employing such compositions.

It is known to dye keratinous fibers, and in particular the hair, with dyeing compositions comprising direct dyes, that is to say coloring molecules having an affinity for the fibers. The dyeing process which employs them is a so-called direct dyeing process, wherein the direct dyes are allowed to stand on the fibers and are then rinsed.

The colorings which result therefrom are temporary or semi-permanent colorings, because the nature of the interactions which bind the direct dyes to the keratinous fiber and their desorption from the surface and/or from the core of the fiber are responsible for their weak dyeing power and their poor ability to withstand washing operations or perspiration.

Cationic nitrophenylenediamines have certainly already been described among known direct dyes but their cationic charge is localized on the nitrogen atom of an aliphatic chain or of a mononitrogenous heterocycle. Such nitrophenylenediamines are disclosed, for example, in British Patent No. 1,164,824 and U.S. Pat. No. 4,018,556, the disclosures of which are incorporated by reference herein.

However, in hair dyeing, there is a constant search for direct dyes which exhibit improved characteristics.

It is therefore after a great deal of research directed at this question that the inventors have now just discovered, entirely unexpectedly and surprisingly, novel cationic monobenzene nitrophenylenediamines with at least one cationic charge delocalized over an unsaturated 5-membered polynitrogenous heterocycle and therefore comprising at least one Z cationic group, Z being chosen from quaternized aliphatic chains, aliphatic chains comprising at least one quaternized saturated ring and aliphatic chains comprising at least one quaternized unsaturated ring.

This novel family of dyes exhibits the highly advantageous distinguishing feature of a greater solubility in dyeing media, and these novel dyes produce colors, by direct coloring, which possess a power and a resistance (to the various attacks which hair may be subject to: light, rubbing, bad weather, shampoos or perspiration) which are significantly improved with respect to those of the colors produced with known cationic nitrophenylenediamines of the prior art, the cationic charge of which is localized on the nitrogen atom of an aliphatic chain or of a mononitrogenous heterocycle.

This discovery forms the basis of the present invention.

The subject of the present invention is thus the cationic monobenzene nitrophenylenediamines of following formula (I):

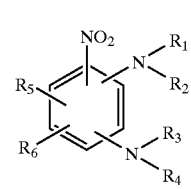

in which formula, $R^1$, $R_2$, $R_3$ and $R_4$, which can be identical or different, represent a hydrogen atom; a Z group defined below; a $(C_1-C_6)$alkyl radical; a monohydroxy$(C_1-C_6)$alkyl radical; a polyhydroxy$(C_2-C_6)$alkyl radical; a $(C_1-C_6)$alkoxy$(C_1-C_6)$alkyl radical; an aryl radical; a benzyl radical; a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a thiocarbamyl$(C_1-C_6)$alkyl radical; a trifluoro-$(C_1-C_6)$alkyl radical; a sulpho$(C_1-C_6)$alkyl radical; a $(C_1-C_6)$alkylcarboxy$(C_1-C_6)$alkyl radical; a $(C_1-C_6)$alkylsulphinyl$(C_1-C_6)$alkyl radical; an aminosulphonyl$(C_1-C_6)$alkyl radical; an N—Z-aminosulphonyl$(C_1-C_6)$alkyl radical; an N—$(C_1-C_6)$alkylaminosulphonyl$(C_1-C_6)$alkyl radical; an N,N-di$(C_1-C_6)$alkylaminosulphonyl$(C_1-C_6)$alkyl radical; a $(C_1-C_6)$alkylcarbonyl$(C_1-C_6)$alkyl radical; an amino$(C_1-C_6)$alkyl radical, the alkyl of which is unsubstituted or substituted by one or more hydroxyl radicals; or an amino$(C_1-C_6)$alkyl radical, the alkyl of which is unsubstituted or substituted by one or more hydroxyl radicals and the amine of which is substituted by one or two identical or different radicals which may together form, with the nitrogen atom to which they are attached, a carbonaceous 5- or 6-membered ring or a 5- or 6-membered ring comprising one or more heteroatoms, or which are chosen from alkyl, monohydroxy$(C_1-C_6)$alkyl, polyhydroxy$(C_2-C_6)$alkyl, $(C_1-C_6)$alkylcarbonyl, carbamyl, N—$(C_1-C_6)$alkylcarbamyl or N,N-di$(C_1-C_6)$alkylcarbamyl, $(C_1-C_6)$alkylsulphonyl, formyl, trifluoro$(C_1-C_6)$alkylcarbonyl, $(C_1-C_6)$alkylcarboxyl or thiocarbamyl radicals, or from a Z group defined below;

$R_5$ and $R_6$, which can be identical or different, represent a hydrogen atom; a halogen atom; a Z group defined below; a $(C_1-C_6)$alkylcarbonyl radical; an amino$(C_1-C_6)$alkylcarbonyl radical; an N—Z-amino$(C_1-C_6)$alkylcarbonyl radical; an N—$(C_1-C_6)$alkylamino$(C_1-C_6)$alkylcarbonyl radical; an N,N-di$(C_1-C_6)$alkylamino$(C_1-C_6)$alkylcarbonyl radical; an amino$(C_1-C_6)$alkylcarbonyl$(C_1-C_6)$alkyl radical; an N—Z-amino$(C_1-C_6)$alkylcarbonyl$(C_1-C_8)$alkyl radical; an N—$(C_1-C_6)$alkylamino$(C_1-C_6)$alkylcarbonyl$(C_1-C_6)$alkyl radical; an N,N-di$(C_1-C_6)$alkylamino$(C_1-C_6)$alkylcarbonyl$(C_1-C_6)$alkyl radical; a carboxyl radical; a $(C_1-C_6)$alkylcarboxyl radical; a $(C_1-C_6)$alkylsulphonyl radical; an aminosulphonyl radical; an N—Z-aminosulphonyl radical; an N—$(C_1-C_6)$alkylaminosulphonyl radical; an N,N-di$(C_1-C_6)$alkylaminosulphonyl radical; an aminosulphonyl$(C_1-C_6)$alkyl radical; an N—Z-aminosulphonyl$(C_1-C_6)$alkyl radical; an N—$(C_1-C_6)$alkylaminosulphonyl$(C_1-C_6)$alkyl radical; an N,N-di$(C_1-C_6)$alkylaminosulphonyl$(C_1-C_6)$alkyl radical; a carbamyl radical; an N—$(C_1-C_6)$alkylcarbamyl radical; an N,N-di$(C_1-C_6)$alkylcarbamyl radical; a carbamyl$(C_1-C_6)$alkyl radical; an N—$(C_1-C_6)$ alkylcarbamyl($C_1$–$C_6$)alkyl radical; an N,N-di($C_1$–$C_6$) alkylcarbamyl($C_1$–$C_6$)alkyl radical; a ($C_1$–$C_6$)alkyl radical; a monohydroxy($C_1$–$C_6$)alkyl radical; a polyhydroxy($C_2$–$C_6$)alkyl radical; a ($C_1$–$C_6$)alkoxy ($C_1$–$C_6$)alkyl radical; a trifluoro($C_1$–$C_6$)alkyl radical; a cyano radical; an $OR_7$ or —$SR_7$ group defined below; or an amino($C_1$–$C_6$)alkyl radical, the alkyl of which is unsubstituted or substituted by one or more hydroxyl radicals and the amine of which is unsubstituted or substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, carbamyl, N—($C_1$–$C_6$)alkylcarbamyl or N,N-di ($C_1$–$C_6$)alkylcarbamyl, ($C_1$–$C_6$)alkylsulphonyl, formyl, trifluoro($C_1$–$C_6$)alkylcarbonyl, ($C_1$–$C_6$) alkylcarboxyl or thiocarbamyl radicals, or from a Z group defined below;

$R_7$ denotes a hydrogen atom; a ($C_1$–$C_6$)alkyl radical; a monohydroxy($C_1$–$C_6$)alkyl radical; a polyhydroxy ($C_2$–$C_6$)alkyl radical; a Z group; a ($C_1$–$C_6$)alkoxy ($C_1$–$C_6$)alkyl radical; an aryl radical; a benzyl radical; a carboxy($C_1$–$C_6$)alkyl radical; a ($C_1$–$C_6$)alkylcarboxy ($C_1$–$C_6$)alkyl radical; a cyano($C_1$–$C_6$)alkyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a trifluoro($C_1$–$C_6$) alkyl radical; an aminosulphonyl($C_1$–$C_6$)alkyl radical; an N—Z-aminosulphonyl($C_1$–$C_6$)alkyl radical; an N—($C_1$–$C_6$)alkylaminosulphonyl($C_1$–$C_6$)alkyl radical; an N,N-da($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$) alkylcarbonyl($C_1$–$C_6$)alkyl radical; an amino($C_1$–$C_6$) alkyl radical, the alkyl of which is unsubstituted or substituted by one or more hydroxyl radicals; or an amino($C_1$–$C_6$)alkyl radical, the alkyl of which is unsubstituted or substituted by one or more hydroxyl radicals and the amine of which is substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$) alkylcarbonyl, ($C_1$–$C_6$)alkylcarboxyl, carbamyl, N—($C_1$–$C_6$)alkylcarbamyl, N,N-di($C_1$–$C_6$) alkylcarbamyl, thiocarbamyl or ($C_1$–$C_6$)alkylsulphonyl radicals, or from a Z group defined below;

Z is chosen from the unsaturated cationic groups of following formulae (II) and (III) and the saturated cationic groups of following formula (IV):

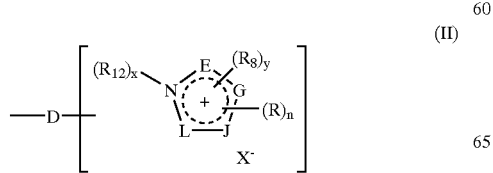

(II)

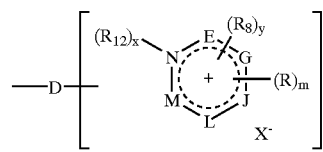

(III)

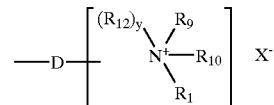

(IV)

in which formulae:

D is a linking arm which represents a linear or branched alkyl chain preferably comprising from 1 to 14 carbon atoms which can be interrupted by one or more heteroatoms, such as oxygen, sulphur or nitrogen atoms, and which can be substituted by one or more hydroxyl or ($C_1$–$C_6$)alkoxy radicals and which can carry one or more ketone functional groups;

the E, G, J, L and M vertices, which are identical or different, represent a carbon, oxygen, sulphur or nitrogen atom;

n is an integer ranging from 0 to 4;

m is an integer ranging from 0 to 5;

the R radicals, which are identical or different, represent a second Z group identical to or different from the first Z group; a halogen atom; a hydroxyl radical; a ($C_1$–$C_6$)alkyl radical; a monohydroxy($C_1$–$C_6$)alkyl radical; a polyhydroxy($C_2$–$C_6$)alkyl radical; a nitro radical; a cyano radical; a cyano($C_1$–$C_6$)alkyl radical; a ($C_1$–$C_6$)alkoxy radical; a tri($C_1$–$C_6$)alkylsilyl ($C_1$–$C_6$)alkyl radical; an amido radical; a formyl radical; a carboxyl radical; a ($C_1$–$C_6$)alkylcarbonyl radical; a thio radical; a thio($C_1$–$C_6$)alkyl radical; a ($C_1$–$C_6$)alkylthio radical; an amino radical; an amino radical protected by a ($C_1$–$C_6$)alkylcarbonyl, carbamyl or ($C_1$–$C_6$)alkylsulphonyl radical; or an NHR' or NR'R'" group in which R' and R'", which are identical or different, represent a ($C_1$–$C_6$)alkyl radical, a monohydroxy($C_1$–$C_6$)alkyl radical or a polyhydroxy($C_2$–$C_6$)alkyl radical;

$R_8$ represents a ($C_1$–$C_6$)alkyl radical; a monohydroxy ($C_1$–$C_6$)alkyl radical; a polyhydroxy($C_2$–$C_6$)alkyl radical; a cyano($C_1$–$C_6$)alkyl radical; a tri($C_1$–$C_6$) alkylsilyl($C_1$–$C_6$)alkyl radical; a ($C_1$–$C_6$)alkoxy ($C_1$–$C_6$)alkyl radical; a carbamyl($C_1$–$C_6$)alkyl radical; a ($C_1$–$C_6$)alkylcarboxy($C_1$–$C_6$)alkyl radical; a benzyl radical; or a second Z group identical to or different from the first Z group;

$R_9$, $R_{10}$ and $R_{11}$, which are identical or different, represent a ($C_1$–$C_6$)alkyl radical; a monohydroxy ($C_1$–$C_6$)alkyl radical; a polyhydroxy($C_2$–$C_6$)alkyl radical; a ($C_1$–$C_6$)alkoxy-($C_1$–$C_6$)alkyl radical; a cyano($C_1$–$C_6$)alkyl radical; an aryl radical; a benzyl radical; an amido($C_1$–$C_6$)alkyl radical; a tri($C_1$–$C_6$) alkylsilyl($C_1$–$C_6$)alkyl radical; or an amino($C_1$–$C_6$) alkyl radical, the amine of which is protected by a ($C_1$–$C_6$)alkylcarbonyl, carbamyl or ($C_1$–$C_6$) alkylsulphonyl radical; two of the $R_9$, $R_{10}$ and $R_{11}$ radicals can also together form, with the nitrogen atom to which they are attached, a saturated carbonaceous 5- or 6-membered ring or a saturated 5- or 6-membered ring which can comprise one or more heteroatoms, such as, for example, a pyrrolidine ring, a piperidine ring, a piperazine ring or a morpholine ring, it being possible for the ring to be unsubstituted or substituted by a halogen atom, a hydroxyl radical, a ($C_1$–$C_6$)alkyl radical, a monohydroxy($C_1$–$C_6$)alkyl radical, a polyhydroxy($C_2$–$C_6$)alkyl radical, a nitro radical, a cyano radical, a cyano($C_1$–$C_6$)alkyl radical, a ($C_1$–$C_6$)alkoxy radical, a tri($C_1$–$C_6$)alkylsilyl($C_1$–$C_6$)alkyl radical, an amido radical, a formyl radical, a carboxyl radical, a keto($C_1$–$C_6$)alkyl radical, a thio radical, a thio($C_1$–$C_6$)alkyl radical, a ($C_1$–$C_6$)alkylthio radical, an amino radical or an amino radical protected by a ($C_1$–$C_6$)alkylcarbonyl, carbamyl or ($C_1$–$C_6$)alkylsulphonyl radical; one of the $R_9$, $R_{10}$ and $R_{11}$ radicals can also represent a second Z group identical to or different from the first Z group;

$R_{12}$ represents a ($C_1$–$C_6$)alkyl radical; a monohydroxy ($C_1$–$C_6$)alkyl radical; a polyhydroxy($C_2$–$C_6$)alkyl radical; an aryl radical; a benzyl radical; an amino ($C_1$–$C_6$)alkyl radical; an amino($C_1$–$C_6$)alkyl radical, the amine of which is protected by a ($C_1$–$C_6$) alkylcarbonyl, carbamyl or ($C_1$–$C_6$)alkylsulphonyl radical; a carboxy($C_1$–$C_6$)alkyl radical; a cyano ($C_1$–$C_6$)alkyl radical; a carbamyl-($C_1$–$C_6$)alkyl radical; a trifluoro($C_1$–$C_6$)alkyl radical; a tri($C_1$–$C_6$) alkylsilyl($C_1$–$C_6$)alkyl radical; a sulphonamido ($C_1$–$C_6$)alkyl radical; a ($C_1$–$C_6$)alkylcarboxy ($C_1$–$C_6$)alkyl radical; a ($C_1$–$C_6$)alkylsulphinyl ($C_1$–$C_6$)alkyl radical; a ($C_1$–$C_6$)alkylsulphonyl ($C_1$–$C_6$)alkyl radical; a ($C_1$–$C_6$)alkylketo($C_1$–$C_6$) alkyl radical; an N—($C_1$–$C_6$)alkylcarbamyl($C_1$–$C_6$) alkyl radical; or an N—($C_1$–$C_6$)alkylsulphonamido ($C_1$–$C_6$)alkyl radical;

x and y are integers equal to 0 or 1; with the following conditions:
in the unsaturated cationic groups of formula (II):
  when x=0, the D linking arm is attached to the nitrogen atom,
  when x=1, the D linking arm is attached to one of the E, G, J or L vertices,
  y can take the value 1 only:
    1) when the E, G, J and L vertices simultaneously represent a carbon atom and when the $R_8$ radical is carried by the nitrogen atom of the unsaturated ring; or else
    2) when at least one of the E, G, J and L vertices represents a nitrogen atom to which the $R_8$ radical is attached;
in the unsaturated cationic groups of formula (III):
  when x=0, the D linking arm is attached to the nitrogen atom,
  when x=1, the D linking arm is attached to one of the E, G, J, L or M vertices,
  y can take the value 1 only when at least one of the E, G, J, L and M vertices represents a divalent atom and when the $R_8$ radical is carried by the nitrogen atom of the unsaturated ring;
in the cationic groups of formula (IV):
  when y=0, then the D linking arm is attached to the nitrogen atom carrying the $R_9$ to $R_{11}$ radicals,
  when y=1, then two of the $R_9$ to $R_{11}$ radicals form, jointly with the nitrogen atom to which they are attached, a saturated 5- or 6-membered ring as defined above and the D linking arm is carried by a carbon atom of the saturated ring;

$X^-$ represents a monovalent or divalent anion and is preferably chosen from a halogen atom, such as chlorine, bromine, fluorine or iodine, a hydroxide, a hydrogen sulphate or a ($C_1$–$C_6$)alkyl sulphate, such as, for example, a methyl sulphate or an ethyl sulphate;

it being understood:
  that the number of Z unsaturated cationic groups of formula (II) in which at least one of the E, G, J and L vertices represents a nitrogen atom is at least equal to 1, and
  that, when one and only one of the $R_1$ to $R_4$ or $R_7$ radicals denotes a Z group in which the D linking arm represents an alkyl chain comprising a ketone functional group, then the ketone functional group is not directly attached to the nitrogen atom of the $NR_1R_2$ or $NR_3R_4$ group or to the oxygen atom of the $OR_7$ group when $R_5$ or $R_6$ represents $OR_7$.

The alkyls and alkoxys mentioned above in the formulae (I), (II), (III) and (IV) can be linear or branched.

The compounds of formula (I) can optionally be salified by strong inorganic acids, such as HCl, HBr or $H_2SO_4$, or organic acids, such as acetic, tartaric, lactic, citric or succinic acid.

Mention may in particular be made, among the rings of the Z unsaturated groups of above formula (II), by way of example, of the pyrrole, imidazole, pyrazole, oxazole, thiazole and triazole rings.

Mention may in particular be made, among the rings of the Z unsaturated groups of above formula (III), by way of example, of the pyridine, pyrimidine, pyrazine, oxazine and triazine rings.

The compounds of formula (I) are preferably chosen from those of following formulae $(I)_1$ to $(I)_{15}$:

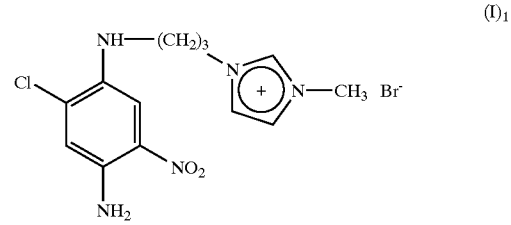

(I)$_1$ i.e., 1-(3-(4-amino-2-chloro-5-nitrophenylamino)propyl)-3-methyl-3H-imidazol-1-ium bromide,

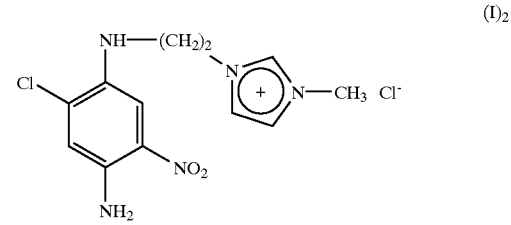

(I)$_2$ i.e., 1-(2-(4-amino-2-chloro-5-nitrophenylamino)ethyl)-3-methyl-3H-imidazol-1-ium chloride,

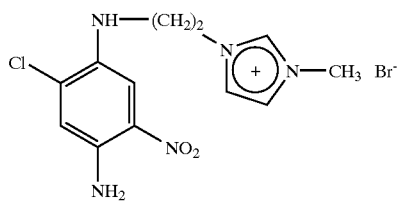

i.e., 1-(2-(4-amino-2-chloro-5-nitrophenylamino)ethyl)-3-methyl-3H-imidazol-1-ium bromide,

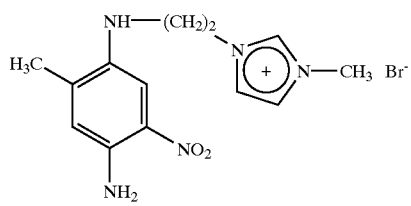

i.e., 1-(2-(4-amino-2-methyl-5-nitrophenylamino)ethyl)-3-methyl-3H-imidazol-1-ium bromide,

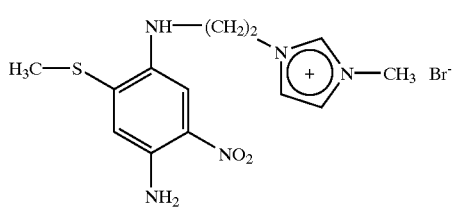

i.e., 1-(2-(4-amino-2-methylsulphanyl-5-nitrophenylamino)ethyl)-3-methyl-3H-imidazol-1-ium bromide,

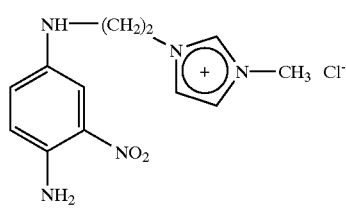

i.e., 1-(2-(4-amino-3-nitrophenylamino)ethyl)-3-methyl-3H-imidazol-1-ium chloride,

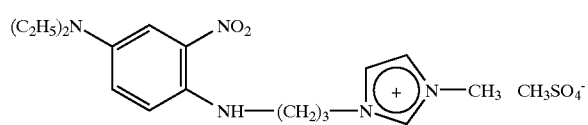

i.e., 3-(3-(4-diethylamino-2-nitrophenylamino)propyl)-1-methyl-3H-imidazol-1-ium methyl sulphate,

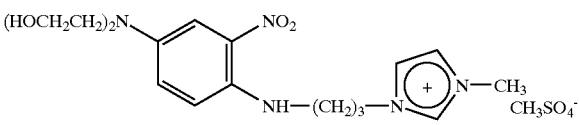

i.e., 3-(3-{4-(bis(2-hydroxyethyl)amino)-2-nitrophenylamino}propyl)-1-methyl-3H-imidazol-1-ium methyl sulphate,

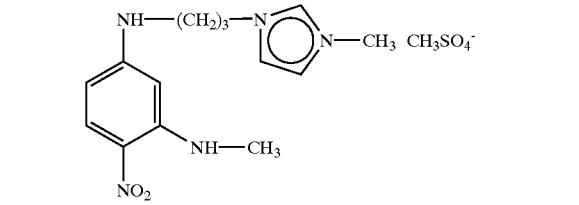

i.e., 1-methyl-3-(3-(3-methylamino-4-nitrophenylamino)propyl)-3H-imidazol-l1-ium methyl sulphate,

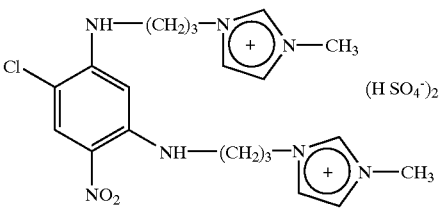

i.e., 3-(3-{2-chloro-5-(3-(3-methyl-3H-imidazol-1-io)propylamino)-4-nitrophenylamino}propyl)-1-methyl-3H-imidazol-1-ium di(hydrogen sulphate),

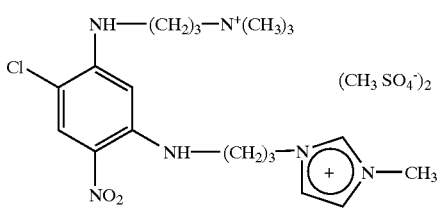

i.e., 3-(3-{4-chloro-5-(3-(trimethylammonio)propylamino)-2-nitrophenyl-amino}propyl)-1-methyl-3H-imidazol-1-ium di(methyl sulphate),

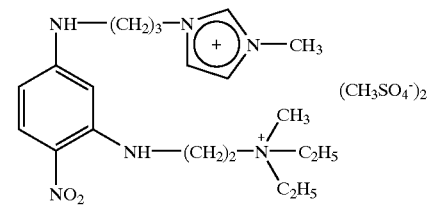

i.e., 3-(3-{3-(2-(diethylmethylammonio)ethylamino)-4-nitrophenylamino}propyl)-1-methyl-3H-imidazol-1-ium di(methyl sulphate),

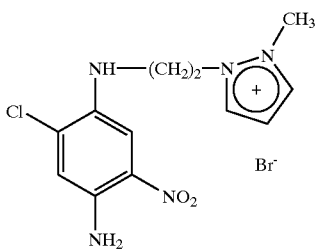

i.e., 1-(2-(4-amino-2-chloro-5-nitrophenylamino)ethyl)-2-methyl-2H-pyrazol-1-ium bromide,

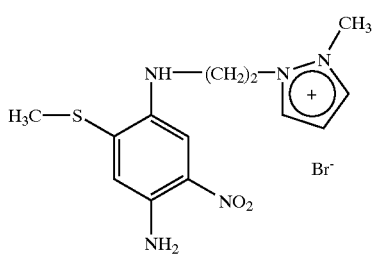

i.e., 1-(2-(4-amino-2-methylsulphanyl-5-nitrophenylamino)ethyl)-2-methyl-2H-pyrazol-1-ium bromide,

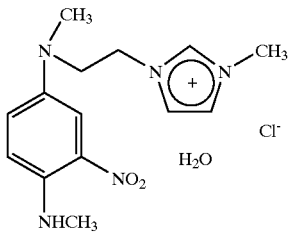

i.e., 3-methyl-1-{2-(methyl(4-methylamino-3-nitrophenyl)amino)ethyl}-3H-imidazol-1-ium chloride monohydrate.

The compounds of formula (I) in accordance with the invention can be easily obtained according to methods generally well known in the state of the art for the preparation of quaternized amines, for example:

in one step, by condensation of a nitrophenylenediamine comprising a haloalkyl radical with a compound carrying a tertiary amine radical or by condensation of a nitrophenylenediamine comprising a tertiary amine radical with a compound carrying a haloalkyl radical;

or, in two steps, by condensation of a nitrophenylenediamine comprising a haloalkyl radical with a compound carrying a secondary amine or by condensation of a halogenated nitrophenylenediamine with a (disubstituted amino)alkylamine, followed by quaternization with an alkylating agent.

The quaternization stage is generally, for convenience, the final stage of the synthesis but can take place earlier in the sequence of reactions resulting in the preparation of the compounds of formula (I).

Another subject of the invention is a dyeing composition for keratinous substances comprising, in a medium appropriate for dyeing, an effective amount of at least one cationic monobenzene nitrophenylenediamine of formula (I) described above.

Another subject of the invention is a composition for the direct dyeing of human keratinous fibers, such as the hair, comprising, in a medium appropriate for dyeing, an effective amount of at least one cationic monobenzene nitrophenylenediamine as defined above by the formula (I).

Another subject of the invention is the use of the cationic monobenzene nitrophenylenediamines of formula (I) as direct dyes in or for the preparation of dyeing compositions for keratinous substances, in particular for human keratinous fibers, such as the hair.

However, other characteristics, aspects and advantages of the invention will become even more clearly apparent on reading the description which will follow and various concrete but in no way limiting examples intended to illustrate it.

The cationic monobenzene nitrophenylenediamine(s) of formula (I) in accordance with the invention and/or their addition salts with an acid preferably represent from 0.005 to 12% by weight approximately of the total weight of the dyeing composition and more preferably still from 0.05 to 6% by weight approximately of this weight.

The cationic monobenzene nitrophenylenediamines of formula (I) in accordance with the invention can also be used, in the well-known oxidation dyeing processes using oxidation dyes (oxidation dye precursors and, optionally, couplers), to shade or enrich with highlights the colors obtained with the oxidation dyes.

The dyeing composition according to the invention can also comprise, in order to widen the palette of shades and to obtain varied hues, in addition to the cationic monobenzene nitrophenylenediamines of formula (I), other conventionally used direct dye(s) and in particular nitrobenzene dyes other than the cationic nitrophenylenediamines of formula (I) according to the present invention, such as nitrodiphenylamines, nitrophenol ethers or nitrophenols, nitropyridines, anthraquinone dyes, nitroanilines, mono- or diazo, triarylmethane, azine, acridine and xanthene dyes or metal complex dyes.

The proportion of all these other additional direct dyes can vary from approximately 0.05 to 10% by weight with respect to the total weight of the dyeing composition.

The medium appropriate for dyeing (or vehicle) is generally composed of water or of a mixture of water and of at least one organic solvent, in order to dissolve the compounds which would not be sufficiently soluble in water. Mention may be made, for example, as organic solvent, of lower $C_1$–$C_4$ alkanols, such as ethanol and isopropanol, glycerol, glycols and glycol ethers, such as 2-butoxyethanol, propylene glycol or propylene glycol monomethyl ether, and aromatic alcohols, such as benzyl alcohol or phenoxyethanol, the analogous products and their mixtures.

The solvents can be present in proportions preferably ranging from 1 to 40% by weight with respect to the total weight of the dyeing composition and more preferably still from 5 to 30% by weight approximately.

Fatty amides, such as the mono- and diethanolamides of the acids derived from copra, of lauric acid or of oleic acid, can also be added to the composition according to the invention at concentrations ranging from approximately 0.05 to 10% by weight.

Surface-active agents well known in the state of the art and of anionic, cationic, nonionic, amphoteric or zwifterionic type or their mixtures can also be added to the composition according to the invention, preferably in a proportion ranging from approximately 0.1 to 50% by weight and advantageously from approximately 1 to 20% by weight with respect to the total weight of the composition.

Thickening agents can also be used in a proportion ranging from approximately 0.2 to 5%.

The dyeing composition can, in addition, comprise various conventional adjuvants, such as antioxidizing agents, fragrances, sequestering agents, dispersing agents, hair conditioning agents, preserving agents, opacifying agents and any other adjuvant commonly used in dyeing keratinous substances.

Of course, a person skilled in the art will take care to choose the optional additional compound or compounds mentioned above so that the advantageous properties intrinsically attached to the dyeing composition according to the invention are not, or not substantially, detrimentally affected by the envisaged addition or additions.

The dyeing composition according to the invention can be formulated at acidic, neutral or alkaline pH, it being possible for the pH to vary from 3 to 12 approximately and preferably from 5 to 11 approximately. It can be adjusted to the desired value by means of acidifying or basifying agents or of buffers commonly used in dyeing keratinous substances.

Acidifying agents are conventionally inorganic or organic acids, such as, for example, hydrochloric acid, orthophosphoric acid or sulphuric acid, carboxylic acids such as acetic acid, tartaric acid, citric acid or lactic acid, and sulphonic acids.

Mention may be made, among buffers, of, for example, potassium dihydrogen phosphate/sodium hydroxide.

Mention may be made, among basifying agents, by way of example, of aqueous ammonia, alkaline carbonates, alkanolamines, such as mono-, di- and triethanolamines, and their derivatives, sodium hydroxide, potassium hydroxide and the compounds of formula:

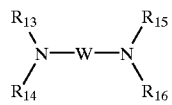

in which W is a propylene residue optionally substituted by a hydroxyl group or a ($C_1$–$C_4$)alkyl radical and $R_{13}$, $R_{14}$, $R_{15}$ and $R_{16}$, simultaneously or independently of one another, represent a hydrogen atom or a ($C_1$–$C_6$)alkyl or hydroxy ($C_1$–$C_6$)alkyl radical.

The dyeing composition according to the invention can be provided in various forms, such as in the form of a liquid, cream or gel or in any other form appropriate for carrying out dyeing of keratinous substances and more particularly of human keratinous fibers and especially of the hair. In particular, it can be packaged under pressure in an aerosol can in the presence of a propellent and can form a foam.

Another subject of the present invention is a process for dyeing keratinous fibers, in particular human keratinous fibers, such as the hair, by direct coloring, which comprises the step of allowing a dyeing composition comprising at least one cationic monobenzene nitrophenylenediamine of formula (I) to act on dry or wet keratinous fibers. The composition according to the invention can be used as a leave-in composition, that is to say that, after application of the composition to the fibers, drying is carried out without intermediate rinsing.

In other methods of application, the composition is allowed to act on the fibers for an exposure time varying from 3 to 60 minutes approximately, preferably from 5 to 45 minutes approximately, rinsing is carried out, washing is optionally carried out, rinsing is then again carried out, and drying is carried out.

Concrete examples illustrating the invention will now be given.

PREPARATION EXAMPLES

Example 1

Preparation of the Compound of Formula $(I)_1$ 1-(3-(4-amino-2-chloro-5-nitrophonylamino)propyl)-3-methyl-3H-imidazol-1-ium bromide
(Delocalized Charge in the Imidazole Ring).

1st Stage:

Synthesis of N-(4-Amino-2-chloro-5-nitrophenyl)-N-(3-bromopropyl)benzenesulphonamide.

A suspension of 98.3 g (0.3 mol) of N-(4-amino-2-chloro-5-nitrophenyl)benzenesulphonamide (RN 84741-80-0) and 25.3 g of calcium oxide in 250 ml of dimethylformamide was heated in a reactor on a refluxing water bath.

61.2 ml (0.6 mol) of 1,3-dibromopropane were added all at once with stirring and the heating was prolonged for one hour.

The reaction mixture was filtered hot and run into 3 kg of ice-cold water; the gum which precipitated was separated by settling and extracted with ethyl acetate.

The ethyl acetate phase was dried over sodium sulphate, filtered and evaporated to dryness under reduced pressure.

The compound obtained was purified by passing through a column of silica gel (heptane and ethyl acetate gradient).

55.8 g of yellow crystals were obtained, which crystals melted at 116° C. (Kofler) and had an elemental analysis, calculated for $C_{15}H_{15}N_3O_4SBrCl$, of:

| %          | C     | H    | N    | O     | S    | Br    | Cl   |
|------------|-------|------|------|-------|------|-------|------|
| Calculated | 40.15 | 3.37 | 9.36 | 14.26 | 7.15 | 17.81 | 7.90 |
| Found      | 40.24 | 3.37 | 9.32 | 14.53 | 6.50 | 17.58 | 7.69 |

2nd Stage:

Synthesis of N1-(3-Bromopropyl)-2-chloro-5-nitrobenzene-1,4-diamine.

The compound obtained in the above stage 1 (55.8 g, 0.125 mol) was introduced portionwise into 170 ml of vigorously stirred 98% sulphuric acid and was maintained between 15° C. and 20° C. with an ice bath.

At the end of the addition, the solution was stirred for an additional hour at 15–20° C. The solution was subsequently poured onto 1 kg of ice and partially neutralized to pH 5 with 20% aqueous ammonia; the crystallized precipitate was filtered off, reslurried in water and dried under vacuum at 40° C. over phosphorus pentoxide.

35.4 g of red crystals were obtained, which crystals, after purification by recrystallization from refluxing isopropyl acetate, melted at 128° C. (Kofler) and had an elemental analysis, calculated for $C_9H_{11}N_3O_2BrCl$, of:

| %          | C     | H    | N     | O     | Br    | Cl    |
|------------|-------|------|-------|-------|-------|-------|
| Calculated | 35.03 | 3.59 | 13.62 | 10.37 | 25.90 | 11.49 |
| Found      | 35.13 | 3.65 | 13.62 | 10.27 | 25.69 | 11.49 |

3rd Stage:

Quaternization of the Compound Prepared in the 2nd Stage.

The suspension of 12.3 g (0.04 mol) of N1-(3-bromopropyl)-2-chloro-5-nitrobenzene-1,4-diamine, obtained in the stage 2, and 3.9 g (0.048 mol) of 1-methyl-1H-imidazole (RN 616-47-7) in 40 ml of toluene was prepared.

The mixture was heated at reflux of the toluene with stirring for 4 hours, filtered off under reflux conditions and reslurried twice in ethyl acetate and then in absolute ethanol.

After drying at 40° C. under vacuum, 15.0 g of dark red crystals of 1-(3-(4-amino-2-chloro-5-nitrophenylamino) propyl)-3-methyl-3H-imidazol-1-ium bromide were obtained, which crystals melt at more than 260° C. (Kofler) and had an elemental analysis, calculated for $C_{13}H_{17}N_5O_2BrCl$, of:

| % | C | H | N | O | Br | Cl |
|---|---|---|---|---|---|---|
| Calculated | 39.87 | 4.39 | 17.93 | 8.19 | 20.45 | 9.07 |
| Found | 39.86 | 4.39 | 18.26 | 8.14 | 20.39 | 8.94 |

Example 2

Preparation of the Compound of Formula $(I)_2$ 1-(2-(4-Amino-2-chloro-5-nitrophenylamino)ethyl)-
3-methyl-3H-imidazol-1-ium Chloride
(Delocalized Charge in the Imidazole Ring).

1st Stage:
Synthesis of N-(4-Amino-2-chloro-5-nitrophenyl)-N-(2-chloroethyl)benzenesulphonamide.

The procedure described in Example 1 (1st stage) was followed.

From 98.3 g (0.3 mol) of N-(4-amino-2-chloro-5-nitrophenyl)benzenesulphonamide (RN 84741-80-0) and from 59.3 g (0.6 mol) of 1,2-dichloroethane, 80.2 g of yellow crystals were obtained, which crystals, after purification by recrystallization from refluxing ethyl acetate, melted at 144° C. (Kofler) and had an elemental analysis, calculated for $C_{14}H_{13}N_3O_4SCl_2$, of:

| % | C | H | N | O | S | Cl |
|---|---|---|---|---|---|---|
| Calculated | 43.09 | 3.36 | 10.77 | 16.40 | 8.22 | 18.17 |
| Found | 43.28 | 3.55 | 10.76 | 16.39 | 7.54 | 17.95 |

2nd Stage:
Synthesis of 2-Chloro-N1-(2-chloroethyl)-5-nitrobenzene-1,4-diamine.

The procedure described in Example 1 (2nd stage) was followed.

From 79.5 g (0.203 mol) of N-(4-amino-2-chloro-5-nitrophenyl)-N-(2-chloroethyl)benzenesulphonamide obtained in the preceding stage, 45.0 g of red-brown crystals were obtained, which crystals, after purification by recrystallization from refluxing toluene, melted at 117° C. (Kofler) and had an elemental analysis, calculated for $C_8H_9N_3O_2Cl_2$, of:

| % | C | H | N | O | Cl |
|---|---|---|---|---|---|
| Calculated | 38.42 | 3.63 | 16.80 | 12.80 | 28.35 |
| Found | 38.85 | 3.68 | 16.70 | 13.47 | 27.40 |

3rd Stage:
Quaternization of the Compound Obtained in the 2nd Stage.
The procedure described in Example 1 (3rd stage) was followed.

From 10.0 g (0.04 mol) of 2-chloro-N1-(2-chloroethyl)-5-nitrobenzene-1,4-diamine obtained in the 2nd stage and from 3.9 g (0.048 mol) of 1-methyl-1H-imidazole (RN 616-47-7), 6.2 g of brick-red crystals were obtained, which crystals melted at 221° C. (Kofler) and had an elemental analysis, calculated for $C_{12}H_{15}N_5O_2Cl_2 + \frac{1}{2}H_2O$, of:

| % | C | H | N | O | Cl |
|---|---|---|---|---|---|
| Calculated | 42.24 | 4.73 | 20.53 | 11.72 | 20.78 |
| Found | 42.53 | 4.56 | 20.49 | 11.50 | 20.87 |

Example 3

Preparation of the Compound of Formula $(I)_3$ 1-(2-(4-Amino-2-chloro-5-nitrophenylamino)ethyl)-
3-methyl-3H-imidazol-1-ium bromide
(Delocalized Charge in the Imidazole Ring).

1st Stage:
Synthesis of N-(4-Amino-2-chloro-5-nitrophenyl)-N-(2-bromoethyl)benzenesulphonamide.

The procedure described in Example 1 (1st stage) was followed.

From 145.5 g (0.44 mol) of N-(4-amino-2-chloro-5-nitrophenyl)benzenesulphonamide (RN 84741-80-0) and from 115 ml (1.32 mol) of 1,2-dibromoethane, yellow crystals were obtained, which crystals, after purification by recrystallization from refluxing 96° ethyl alcohol, melted at 115° C. (Kofler) and had an elemental analysis, calculated for $C_{14}H_{13}N_3O_4SBrCl$, of:

| % | C | H | N | O | S |
|---|---|---|---|---|---|
| Calculated | 38.68 | 3.01 | 9.67 | 14.72 | 7.38 |
| Found | 38.83 | 3.15 | 9.55 | 14.87 | 6.55 |

2nd Stage:
Synthesis of N1-(2-Bromoethyl)-2-chloro-5-nitrobenzene-1,4-diamine.

The procedure described in Example 1 (2nd stage) was followed.

From 191.0 g (0.44 mol) of N-(4-amino-2-chloro-5-nitrophenyl)-N-(2-bromoethyl)benzenesulphonamide obtained in the preceding stage, 114.5 g of dark red crystals were obtained, which crystals, after purification by recrystallization from refluxing isopropyl acetate, melted at 120° C. (Kofler) and had an elemental analysis, calculated for $C_8H_9N_3O_2BrCl$, of:

| % | C | H | N | O | Br | Cl |
|---|---|---|---|---|---|---|
| Calculated | 32.62 | 3.08 | 14.27 | 10.86 | 27.13 | 12.04 |
| Found | 32.78 | 3.08 | 14.20 | 10.98 | 27.03 | 12.30 |

3rd Stage:
Quaternization of the Compound Obtained in the 2nd Stage.
The procedure described in Example 1 (3rd stage) was followed.

From 11.8 g (0.04 mol) of N1-(2-bromoethyl)-2-chloro-5-nitrobenzene-1,4-diamine obtained in the preceding stage and from 3.9 g (0.048 mol) of 1-methyl-1H-imidazole (RN 616-47-7), 11.9 g of brick-red crystals were obtained, which crystals melted at 224° C. (Kofler) and had an elemental analysis, calculated for $C_{12}H_{15}N_5O_2BrCl$, of:

| %          | C     | H    | N     | O    | Br    | Cl   |
|------------|-------|------|-------|------|-------|------|
| Calculated | 38.27 | 4.01 | 18.59 | 8.50 | 21.21 | 9.41 |
| Found      | 38.11 | 4.04 | 18.33 | 8.79 | 20.87 | 9.48 |

Example 4

Preparation of the Compound of Formula $(I)_4$ 1-(2-(4-Amino-2-methyl-5-nitrophonylamino)ethyl)-3-methyl-3H-imidazol-1-ium bromide
(Delocalized Charge in the Imidazole Ring).
1st Stage:
Synthesis of N-(4-Amino-2-methyl-5-nitrophenyl)-N-(2-bromoethyl)-4-methylbenzenesulphonamide.

The procedure described in Example 1 (1st stage) was followed.

From 57.0 g (0.177 mol) of N-(4-amino-2-methyl-5-nitrophenyl)-4-methylbenzenesulphonamide (RN 82576-78-1) and from 38.2 ml (0.44 mol) of 1,2-dibromoethane, 66.0 g of yellow crystals were obtained, which crystals, after purification by recrystallization from refluxing ethyl acetate, melted at 159° C. (Kofler) and had an elemental analysis, calculated for $C_{16}H_{18}N_3O_4SBr$, of:

| %          | C     | H    | N    | O     | S    | Br    |
|------------|-------|------|------|-------|------|-------|
| Calculated | 44.87 | 4.24 | 9.81 | 14.94 | 7.49 | 18.66 |
| Found      | 44.79 | 4.25 | 9.62 | 14.93 | 7.05 | 18.48 |

2nd Stage:
Synthesis of N1-(2-Bromoethyl)-2-methyl-5-nitrobenzene-1,4-diamine.

The procedure described in Example 1 (2nd stage) was followed.

From 66.0 g (0.154 mol) of N-(4-amino-2-methyl-5-nitrophenyl)-N-(2-bromoethyl)-4-methylbenzenesulphonamide obtained in the preceding stage, 36.0 g of red-brown crystals were obtained, which crystals, after purification by recrystallization from refluxing isopropyl acetate, melted at 120° C. (Kofler) and had an elemental analysis, calculated for $C_9H_{12}N_3O_2Br$, of:

| %          | C     | H    | N     | O     | Br    |
|------------|-------|------|-------|-------|-------|
| Calculated | 39.44 | 4.41 | 15.33 | 11.67 | 29.15 |
| Found      | 38.55 | 4.44 | 5.00  | 11.60 | 29.37 |

3rd Stage:
Quaternization of the Compound Obtained in the 2nd Stage.

The procedure described in Example 1 (3rd stage) was followed.

From 11.0 g (0.04 mol) of N1-(2-bromoethyl)-2-methyl-5-nitrobenzene-1,4-diamine obtained in the preceding stage and from 3.9 g (0.048 mol) of 1-methyl-1H-imidazole (RN 616-47-7) in isobutanol, 9.9 g of red-brown crystals were obtained, which crystals melted at 200° C. (Kofler) and had an elemental analysis, LAW OFFICES calculated for $C_{13}H_{18}N_5O_2Br$, of:

| %          | C     | H    | N     | O     | Br    |
|------------|-------|------|-------|-------|-------|
| Calculated | 43.83 | 5.09 | 19.66 | 11.67 | 22.43 |
| Found      | 45.37 | 5.24 | 19.45 | 10.18 | 19.78 |

Example 5

Preparation of the Compound of Formula $(I)_5$ 1-(2-(4-Amino-2-methylsulphanyl-5-nitrophenylamino)ethyl)-3-methyl-3H-imidazol-1-ium Bromide
(Delocalized Charge in the Imidazole Ring).
1st Stage:
Synthesis of N-(4-Amino-2-methylsulphanyl-5-nitrophenyl)benzenesulphonamide.

132 g (0.662 mol) of 2-methylsulphanyl-5-nitrobenzene-1,4-diamine (RN 171968-54-0) were dissolved at room temperature in 400 ml of pyridine in a reactor.

120.8 g (0.684 mol) of benzenesulphonyl chloride were run in dropwise with stirring while maintaining the exothermic reaction between 40° C. and 45° C.; the red solution became orange-yellow over ½ hour; it was poured onto 2.7 kg of ice and acidification was carried out with 400 ml of 36% hydrochloric acid.

The ochre-yellow crystallized precipitate obtained was filtered off, reslurried in water to neutrality and dried under vacuum at 40° C. over phosphorus pentoxide.

Yellow crystals were obtained, which crystals, after recrystallization from refluxing acetonitrile, melted at 212° C. (Kofler) and had an elemental analysis, calculated for $C_{13}H_{13}N_3O_4S_2$, of:

| %          | C     | H    | N     | O     | S     |
|------------|-------|------|-------|-------|-------|
| Calculated | 46.01 | 3.86 | 12.38 | 18.86 | 18.89 |
| Found      | 45.94 | 3.86 | 12.35 | 18.61 | 18.24 |

2nd Stage:
Synthesis of N-(4-Amino-2-methylsulphanyl-5-nitrophenyl)-N-(2-bromoethyl)benzenesulphonamide.

The procedure described in Example 1 (1st stage) was followed.

From 116.0 g (0.33 mol) of N-(4-amino-2-methylsulphanyl-5-nitrophenyl)benzenesulphonamide obtained in the preceding stage and from 57.0 ml (0.66 mol) of 1,2-dibromoethane, yellow crystals were obtained, which crystals, after purification by recrystallization from refluxing methyl ethyl ketone, melted at 216° C. (Kofler) and had an elemental analysis, calculated for $C_{15}H_{16}N_3O_4S_2Br$, of:

| %          | C      | H    | N    | O     | S     | Br    |
|------------|--------|------|------|-------|-------|-------|
| Calculated | 40.374 | 3.61 | 9.41 | 14.34 | 14.37 | 17.90 |
| Found      | 0.23   | 3.73 | 9.10 | 15.19 | 13.55 | 17.84 |

3rd Stage:
Synthesis of N1-(2-Bromoethyl)-2-methylsulphanyl-5-nitrobenzene-1,4-diamine.

The procedure described in Example 1 (2nd stage) was followed.

From 147.3 g (0.33 mol) of N-(4-amino-2-methylsulphanyl-5-nitrophenyl)-N-(2-bromoethyl)benzenesulphonamide obtained in the preceding stage, 72.0 g of red crystals were obtained, which crystals, after purification by recrystallization from refluxing ethyl acetate, melted at 131° C. (Kofler) and had an elemental analysis, calculated for $C_9H_{12}N_3O_2SBr$, of:

| %          | C     | H    | N     | O     | S     | Br    |
|------------|-------|------|-------|-------|-------|-------|
| Calculated | 35.31 | 3.95 | 13.72 | 10.45 | 10.47 | 26.10 |
| Found      | 35.56 | 4.06 | 13.72 | 10.57 | 10.14 | 26.39 |

4th Stage:
Quaternization of the Compound Obtained in the 3rd Stage.

The procedure described in Example 1 (3rd stage) was followed.

From 12.2 g (0.04 mol) of N1-(2-bromoethyl)-2-methylsulphanyl-5-nitrobenzene-1,4-diamine obtained in the preceding stage and from 3.9 g (0.048 mol) of 1-methyl-1H-imidazole (RN 616-47-7) in toluene, 11.0 g of brick-red crystals were obtained, which crystals melted at 196° C. (Kofler) and had an elemental analysis, calculated for $C_{13}H_{18}N_5O_2SBr + \frac{1}{2}H_2O$, of:

| %          | C     | H    | N     | O     | S    | Br    |
|------------|-------|------|-------|-------|------|-------|
| Calculated | 39.30 | 4.82 | 17.63 | 10.07 | 8.07 | 20.11 |
| Found      | 40.44 | 4.69 | 17.49 | 9.44  | 8.56 | 18.96 |

Example 6

Preparation of the Compound of Formula $(I)_6$ 1-(2-(4-Amino-3-nitrophenylamino)ethyl)-3-methyl-3H-imidazol-1-ium Chloride
(Delocalized Charge in the Imidazole Ring).

â 1st Stage:
Synthesis of N-(4-Amino-3-nitrophenyl)-N-(2-chloroethyl)-4-methylbenzenesulphonamide.

The procedure described in Example 1 (1st stage) was followed.

From 23.0 g (0.075 mol) of N-(4-amino-3-nitrophenyl)-4-methylbenzenesulphonamide (RN 59457-54-4) and from 29.7 g (0.3 mol) of 1,2-dichloroethane, yellow crystals were obtained, which crystals, after purification by recrystallization from refluxing 96° ethyl alcohol, melted at 146° C. (Kofler) and had an elemental analysis, calculated for $C_{15}H_{16}N_3O_4SCl$, of:

| %          | C     | H    | N     | O     | S    | Cl   |
|------------|-------|------|-------|-------|------|------|
| Calculated | 48.72 | 4.36 | 11.36 | 17.30 | 8.67 | 9.59 |
| Found      | 48.89 | 4.38 | 11.29 | 17.43 | 8.64 | 9.72 |

â 2nd Stage:
Synthesis of N4-(2-Chloroethyl)-2-nitrobenzene-1,4-diamine and Quaternization.

The procedure described in Example 1 (2nd stage) was followed.

From 136.0 g (0.365 mol) of N-(4-amino-3-nitrophenyl)-N-(2-chloroethyl)-4-methylbenzenesulphonamide obtained in the preceding stage, 75.7 g of red-brown crystals of N4-(2-chloroethyl)-2-nitrobenzene-1,4-diamine were obtained, which crystals, after purification by recrystallization from refluxing benzene, melted at 107° C. (Kofler).

For the quaternization, the procedure described in Example 1 (3rd stage) was followed.

From 10.8 g (0.05 mol) of N4-(2-chloroethyl)-2-nitrobenzene-1,4-diamine obtained above and from 4.9 g (0.06 mol) of 1-methyl-1H-imidazole (RN 616-47-7) in toluene, 11.5 g of red-brown crystals were obtained, which crystals melted at 204° C. and had an elemental analysis, calculated for $C_{12}H_{16}N_5O_2Cl + \frac{1}{2}H_2O$, of:

| %          | C      | H    | N     | O     | Cl    |
|------------|--------|------|-------|-------|-------|
| Calculated | 47.694 | 5.50 | 23.17 | 11.91 | 11.73 |
| Found      | 7.52   | 5.50 | 23.20 | 11.98 | 11.85 |

Example 7

Preparation of the Compound of Formula $(I)_7$ 3-(3-(4-diethylamino-2-nitrophenylamino)propyl)-1-methyl-3H-imidazol-1-ium Methyl Sulphate
(Delocalized Charge in the Imidazole Ring).

â 1st Stage:
Synthesis of Diethyl(4-fluoro-3-nitrophenyl)amine.

197 ml (1.5 mol) of diethyl sulphate were run, over 2 hours, with stirring, into a mixture, heated at 65° C., comprising 63.0 g (0.5 mol) of 4-fluoro-3-nitrophenylamine (RN 364-76-1) and 110 g of calcium carbonate in 150 ml of dimethylformamide and then the mixture was heated at 85° C.–90° C. for 2 hours.

The mixture was filtered hot and run into 2 kg of ice-cold water.

The oil which separated by settling was extracted with ethyl acetate; the ethyl acetate extract was dried over sodium sulphate, filtered and evaporated to dryness under reduced pressure.

46.3 g of an orange-red oil were obtained, which oil crystallized (M.p. <50° C., Kofler) after purification by passing through a column of silica gel (heptane and ethyl acetate gradient) and had an elemental analysis, calculated for $C_{10}H_{13}N_2O_2F$, of:

| %          | C     | H    | N     | F    |
|------------|-------|------|-------|------|
| Calculated | 56.60 | 6.17 | 13.20 | 8.95 |
| Found      | 56.47 | 6.22 | 13.20 | 8.91 |

â 2nd Stage:
Synthesis of N4,N4-Diethyl-N1-(3-(imidazol-1-yl)propyl)-2-nitrobenzene-1,4-diamine.

A mixture of 8.8 g (0.041 mol) of diethyl(4-fluoro-3-nitrophenyl)amine obtained in the preceding stage, 17.0 g (0.136 mol) of 3-(imidazol-1-yl)propylamine (RN 5036-48-6) and 6.7 ml of triethylamine was heated at reflux with stirring for 2 hours.

The mixture was poured onto 100 g of ice-cold water; the oil which separated by settling was extracted with ethyl acetate. The ethyl acetate extract was then dried over sodium sulphate, filtered and evaporated to dryness under reduced pressure.

12.8 g of a purple oil were obtained, which oil crystallized (M.p.>260° C., Kofler) after purification by passing through a column of silica gel (heptane and ethyl acetate gradient) and had an elemental analysis, calculated for $C_{16}H_{23}N_5O_2$, of:

| %          | C     | H    | N     | O     |
|------------|-------|------|-------|-------|
| Calculated | 60.55 | 7.30 | 22.07 | 10.08 |
| Found      | 60.39 | 7.29 | 22.05 | 10.20 |

3rd Stage:
Quaternization of the Compound Obtained in the 2nd Stage.

The suspension of 6.3 g (0.02 mol) of N4,N4-diethyl-N1-(3-(imidazol-1-yl)propyl)-2-nitrobenzene-1,4-diamine obtained in the preceding stage and 2.09 ml (0.022 mol) of dimethyl sulphate in 100 ml of ethyl acetate was prepared and was left for 3 hours at room temperature with stirring.

The crystallized precipitate obtained was filtered off, washed several times in ethyl acetate and dried at 50° C. under vacuum.

8.2 g of dark purple crystals were obtained, which crystals melted at 101° C. (Kofler) and had an elemental analysis, calculated for $C_{18}H_{29}N_5O_6S$, of:

| %          | C     | H    | N     | O     | S    |
|------------|-------|------|-------|-------|------|
| Calculated | 48.75 | 6.59 | 15.79 | 21.64 | 7.23 |
| Found      | 48.50 | 6.66 | 15.79 | 22.16 | 7.21 |

Example 8

Preparation of the Compound of Formula $(I)_8$ 3-(3-{4-(bis(2-Hydroxyethyl)amino)-2-nitrophenylamino}propyl)-1-methyl-3H-imidazol-1-ium Methyl Sulphate
(Delocalized Charge in the Imidazole Ring).
â 1st Stage:
Synthesis of 2-{(2-Hydroxyethyl)(4-(3-(imidazol-1-yl)propylamino)-3-nitrophenyl)amino}ethanol.

The procedure described in Example 7 (2nd stage) was used.

From 29.3 g (0.12 mol) of 2-((4-fluoro-3-nitrophenyl)(2-hydroxyethyl)amino)ethanol (RN 29705-38-2) and from 50.0 g (0.4 mol) of 3-(imidazol-1-yl)propylamine (RN 5036-48-6), 39.0 g of purple crystals were obtained, which crystals, after purification by recrystallization from refluxing 96° ethyl alcohol, melted at 141° C. (Kofler) and had an elemental analysis, calculated for $C_{16}H_{23}N_5O_4$, of:

| %          | C     | H    | N     | O     |
|------------|-------|------|-------|-------|
| Calculated | 55.00 | 6.64 | 20.04 | 18.32 |
| Found      | 54.77 | 6.37 | 20.35 | 18.39 |

â 2nd Stage:
Quaternization of the Compound Obtained in the 1st Stage.

The procedure described in Example 7 (3rd stage) was followed.

From 14.0 g (0.04 mol) of 2-{(2-hydroxyethyl)(4-(3-(imidazol-1-yl)propylamino)-3-nitrophenyl)amino}ethanol obtained in the preceding stage and from 4.2 ml (0.044 mol) of dimethyl sulphate, 17.9 g of purple-blue oil were obtained, the elemental analysis of which, calculated for $C_{18}H_{29}N_5O_8S+\frac{1}{2}H_2O$, was:

| %          | C     | H    | N     | O     | S    |
|------------|-------|------|-------|-------|------|
| Calculated | 44.62 | 6.24 | 14.45 | 28.07 | 6.62 |
| Found      | 44.49 | 6.54 | 13.88 | 28.22 | 6.67 |

Example 9

Preparation of the Compound of Formula $(I)_9$

1-Methyl-3-(3-(3-methylamino-4-nitrophenylamino)propyl)-3H-imidazol-1-ium Methyl Sulphate
(Delocalized Charge in the Imidazole Ring).
â 1st Stage:
Synthesis of N1-(3-(Imidazol-1-yl)propyl)N3-methyl-4-nitrobenzene-1,3-diamine.

The procedure described in Example 7 (2nd stage) was followed.

From 37.3 g (0.2 mol) of (5-chloro-2-nitrophenyl)methylamine (RN 35966-84-8) and from 37.5 g (0.3 mol) of 3-(imidazol-1-yl)propylamine (RN 5036-48-6), yellow crystals (52.0 9) were obtained, which crystals, after purification by recrystallization from refluxing 96° ethyl alcohol, melted at 145° C. (Kofler) and had an elemental analysis, calculated for $C_{13}H_{17}N_5O_2$, of:

| %          | C     | H    | N     | O     |
|------------|-------|------|-------|-------|
| Calculated | 56.72 | 6.22 | 25.44 | 11.62 |
| Found      | 56.64 | 6.34 | 25.37 | 11.66 |

â 2nd Stage:
Quaternization of the Compound Obtained in the 1st Stage.

The procedure described in Example 7 (3rd stage) was followed.

From 8.2 g (0.03 mol) of N1-(3-(imidazol-1-yl)propyl)-N3-methyl-4-nitrobenzene-1,3-diamine obtained in the preceding stage and from 3.2 ml (0.034 mol) of dimethyl sulphate, 11.9 g of yellow crystals were obtained, which crystals melted at 120° C. (Kofler) and had an elemental analysis, calculated for $C_{15}H_{23}N_5O_6S$, of:

| %          | C     | H    | N     | O     | S    |
|------------|-------|------|-------|-------|------|
| Calculated | 44.88 | 5.77 | 17.45 | 23.91 | 7.99 |
| Found      | 44.75 | 5.80 | 17.61 | 24.12 | 7.90 |

Example 10

Preparation of the Compound of Formula $(I)_{10}$ 3-(3-{2-Chloro-5-(3-(3-methyl-3H-imidazol-1-io)propylamino)-4-nitrophenylamino}propyl)-1-methyl-3H-imidazol-1-ium Di(hydrogen Sulphate)
(Delocalized Charge in the Imidazole Ring).
â 1st Stage:
Synthesis of 4-Chloro-N1,N3-bis(3-(imidazol-1-yl)propyl)-6-nitrobenzene-1,3-diamine.

A mixture of 113.2 g (0.5 mol) of 1,2,4-trichloro-5-nitrobenzene (RN 89-69-0), 250.4 g (2 mol) of 3-(imidazol-1-yl)propylamine (RN 5036-48-6) and 138 g (1 mol) of calcium carbonate in 660 ml of dioxane was heated at reflux with stirring for 9 hours.

The mixture was poured into 3.3 l of ice-cold water and the crystallized precipitate was filtered off, reslurried in water and dried under vacuum at 50° C. over phosphorus pentoxide.

After purification by recrystallization from refluxing absolute alcohol, 139.3 g of yellow crystals were obtained, which crystals melted at 108–110° C. (Kofler) and had an elemental analysis, calculated for $C_{18}H_{22}N_7O_2Cl+1.5H_2O$, of:

| % | C | H | N | O | Cl |
|---|---|---|---|---|---|
| Calculated | 50.17 | 5.85 | 22.75 | 13.00 | 8.23 |
| Found | 50.57 | 6.07 | 22.85 | 13.10 | 8.00 |

â 2nd Stage:

Quaternization of the Compound Obtained in the 1st Stage.

The procedure described in Example 7 (3rd stage) was followed.

From 21.5 g (0.05 mol) of 4-chloro-N1,N3-bis(3-(imidazol-1-yl)propyl)-6-nitrobenzene-1,3-diamine crystallized with 1.5 molecules of water obtained in the preceding stage and from 14.3 g (0.113 mol) of dimethyl sulphate, and after reslurrying in absolute alcohol warmed to 30° C., 12.0 g of yellow crystals were obtained, which crystals melt at 188–190° C. (Kofler) and had an elemental analysis, calculated for $C_{20}H_{30}N_7O_{10}S_2Cl$, of:

| % | C | H | N | O | Cl | S |
|---|---|---|---|---|---|---|
| Calculated | 38.25 | 4.81 | 15.61 | 25.47 | 5.64 | 10.21 |
| Found | 37.90 | 4.88 | 15.46 | 25.42 | 5.45 | 10.23 |

Example 11

Preparation of the Compound of Formula $(I)_{15}$

3-Methyl-1-{2-(methyl(4-methylamino-3-nitrophenyl)amino)ethyl}-3H-imidazol-1-ium Chloride Monohydrate (Delocalized Charge in the Imidazole Ring).

The procedure described in Example 1 (3rd stage) was followed.

From 41.4 g (0.17 mol) of N4-(2-chloroethyl)-N1,N4-dimethyl-2-nitrobenzene-1,4-diamine (RN 14607-54-6) and from 41.8 g (0.51 mol) of 1-methyl-1H-imidazole (RN 616-47-7) in 100 ml of toluene, 37.8 g of purple crystals of 3-methyl-1-{2-(methyl(4-methylamino-3-nitrophenyl)amino)ethyl}-3H-imidazol-1-ium chloride monohydrate were obtained after recrystallization from refluxing ethanol, which crystals melted at 135° C. (Kofler) and had an elemental analysis, calculated for $C_{14}H_{20}N_5O_2Cl+H_2O$, of:

| % | C | H | N | O | Cl |
|---|---|---|---|---|---|
| Calculated | 48.91 | 6.45 | 20.37 | 13.96 | 10.31 |
| Found | 48.65 | 6.50 | 20.29 | 14.00 | 10.28 |

EXAMPLES OF DYEING COMPOSITIONS

Example 1

The following dyeing composition was prepared:
(All Contents Expressed in Grams—A.M. Denotes Active Material)

| | |
|---|---|
| Dye of formula $(I)_9$ | 0.344 |
| Hydroxyethylcellulose, sold under the name NATROSOL 250 MR by the company Aqualon | 0.72 |
| Benzyl alcohol | 4 |
| Polyethylene glycol with 6 ethylene oxide units | 6 |
| $(C_8-C_{10})$alkyl polyglucoside as an aqueous solution comprising 60% of A.M., sold under the name ORAMIX CG 110 by the company Seppic | 4.5 A.M. |
| Phosphate buffer, pH 9 (boric acid/potassium chloride/sodium hydroxide   q.s. for | 100 |

The above composition was applied to locks of natural or permed grey hair comprising 90% white hairs and was left to stand for 20 minutes. After rinsing with ordinary water and drying, the hair was dyed in an iridescent purple shade.

Examples 2 to 7

The following six dyeing compositions were prepared:
(All Contents Expressed in Grams)

| | EXAMPLE | | | | | |
|---|---|---|---|---|---|---|
| | 2 | 3 | 4 | 5 | 6 | 7 |
| Compound of formula $(I)_1$ | 0.298 | | | | | |
| Compound of formula $(I)_2$ | | 0.356 | | | | |
| Compound of formula $(I)_3$ | | | 0.377 | | | |
| Compound of formula $(I)_4$ | | | | 0.332 | | |
| Compound of formula $(I)_5$ | | | | | 0.391 | |
| Compound of formula $(I)_6$ | | | | | | 0.385 |
| Ethylene glycol monoethyl ether | 10 | 10 | 10 | 10 | 10 | 10 |
| Cetyl/stearyl alcohol/sodium lauryl sulphate mixture, sold under the name SINNOWAX SX by the company Henkel | 2 | 2 | 2 | 2 | 2 | 2 |
| Oxyethylenated (3 EO) linear fatty alcohol $(C_{13}-C_{15})$, sold under the name SYNPERONIC | 3 | 3 | 3 | 3 | 3 | 3 |

-continued

| | EXAMPLE | | | | | |
|---|---|---|---|---|---|---|
| | 2 | 3 | 4 | 5 | 6 | 7 |
| A3 by the company I.C.I. Oxyethylenated (7 EO) linear fatty alcohol ($C_{13}$–$C_{15}$), sold under the name SYNPERONIC A7 by the company I.C.I. | 2 | 2 | 2 | 2 | 2 | 2 |
| Trimethylcetyl-ammonium bromide | 1.5 | 1.5 | 1.5 | 1.5 | 1.5 | 1.5 |
| Monoethanol-amine q.s. pH | 8 | 8 | 8 | 8 | 8 | 8 |
| Demineralized water q.s. for | 100 | 100 | 100 | 100 | 100 | 100 |

Each of the above compositions was applied to locks of permed grey hair comprising 90% white hairs and was left to stand for 20 minutes. After rinsing with ordinary water and drying, the hair was dyed in a shade which is expressed in the table below.

| | |
|---|---|
| Composition of Example 2 | tending towards deep purple |
| Composition of Example 3 | slightly red iridescent |
| Composition of Example 4 | coppery red |
| Composition of Example 5 | coppery red |
| Composition of Example 6 | slightly coppery iridescent |
| Composition of Example 7 | coppery |

Examples 8 and 9

The following two dyeing compositions were prepared:
(All Contents Expressed in Grams)

| EXAMPLE | 8 | 9 |
|---|---|---|
| Compound of formula $(I)_8$ | 0.356 | |
| Compound of formula $(I)_9$ | | 0.344 |
| Oleic diethanolamide | 3 | 3 |
| Lauric acid | 1 | 1 |
| Ethylene glycol monoethyl ether | 5 | 5 |
| Hydroxyethylcellulose | 2 | 2 |
| 2-Amino-2-methyl-1-propanol q.s. pH | 9.5 | 9.5 |
| Demineralized water q.s. for | 100 | 100 |

Each of the above compositions was applied to locks of permed grey hair comprising 90% white hairs and was left to stand for 20 minutes. After rinsing with ordinary water and drying, the hair was dyed in a shade which is expressed in the table below.

| | |
|---|---|
| Composition of Example 8 | purple |
| Composition of Example 9 | purple |

What is claimed is:

1. A compound chosen from cationic monobenzene nitro-phenylenediamines of formula (I) and acid addition salts thereof:

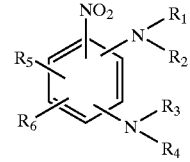

wherein:

$R_1$, $R_2$, $R_3$ and $R_4$, which can be identical or different, are chosen from a hydrogen atom; a Z group as defined below; a ($C_1$–$C_6$)alkyl radical; a mono-hydroxy ($C_1$–$C_6$)alkyl radical; a polyhydroxy($C_2$–$C_6$)alkyl radical; a ($C_1$–$C_6$)alkoxy($C_1$–$C_6$)alkyl radical; an aryl radical; a benzyl radical; a cyano($C_1$–$C_6$)alkyl radical; a carbamyl($C_1$–$C_6$)alkyl radical; an N—($C_1$–$C_6$)alkylcarbamyl($C_1C_6$)alkyl radical; an N,N-di($C_1$–$C_6$)alkylcarbamyl($C_1$–$C_6$)alkyl radical; a thiocarbamyl ($C_1$–$C_6$)alkyl radical; a trifluoro($C_1$–$C_6$)alkyl radical; a sulpho($C_1$–$C_6$)alkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; an aminosulphonyl($C_1$–$C_6$)alkyl radical; an N—Z-aminosulphonyl($C_1$–$C_6$)alkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylcarbonyl($C_1$–$C_6$)alkyl radical; an amino($C_1$–$C_6$)alkyl radical, wherein the alkyl is unsubstituted or substituted by one or more hydroxyl radicals; and an amino($C_1$–$C_6$)alkyl radical, wherein the alkyl is unsubstituted or substituted by one or more hydroxyl radicals and the amine is substituted by one or two identical or different radicals which may together form, with the nitrogen atom to which they are respectively attached, a carbonaceous 5- or 6-membered ring or a 5- or 6-membered ring comprising one or more heteroatoms, or which are chosen from alkyl, monohydroxy($C_1$–$C_6$)alkyl, polyhydroxy($C_2$–$C_6$)alkyl, ($C_1$–$C_6$)alkylcarbonyl, carbamyl, N—($C_1$–$C_6$) alkylcarbamyl or N,N-di($C_1$–$C_6$)alkylcarbamyl, ($C_1$–$C_6$)alkylsulphonyl, formyl, trifluoro($C_1$–$C_6$) alkylcarbonyl, ($C_1$–$C_6$)alkylcarboxyl and thiocarbamyl radicals, and from a Z group as defined below;

$R_5$ and $R_6$, which can be identical or different, are chosen from a hydrogen atom; a halogen atom; a Z group as defined below; a ($C_1$–$C_6$)alkylcarbonyl radical; an amino($C_1$–$C_6$)alkylcarbonyl radical; an N—Z-amino ($C_1$–$C_6$)alkylcarbonyl radical; an N—($C_1$–$C_6$) alkylamino($C_1$–$C_6$)alkylcarbonyl radical; an N,N-di ($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N—Z-aminosulphonyl radical; an N—($C_1$–$C_6$) alkylaminosulphonyl radical; an N,N-di($C_1$–$C_6$) alkylaminosulphonyl radical; an aminosulphonyl ($C_1$–$C_6$)alkyl radical; an N—Z-aminosulphonyl ($C_1$–$C_6$)alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical: a carbamyl($C_1$–$C_6$)alkyl radical; an N—($C_1$–$C_6$)

alkylcarbamyl($C_1$–$C_6$)alkyl radical; an N,N-di($C_1$–$C_6$) alkylcarbamyl($C_1$–$C_6$)alkyl radical; a ($C_1$–$C_6$)alkyl radical; a monohydroxy($C_1$–$C_6$)alkyl radical; a polyhydroxy($C_2$–$C_6$)alkyl radical; a ($C_1$–$C_6$)alkoxy ($C_1$–$C_6$)alkyl radical; a trifluoro($C_1$–$C_6$)alkyl radical; a cyano radical; an $OR_7$ or —$SR_7$ group wherein $R_7$ is as defined below; and an amino($C_1$–$C_6$)alkyl radical, wherein the alkyl is unsubstituted or substituted by one or more hydroxyl radicals and the amine is unsubstituted or substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, carbamyl, N—($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, and from a Z group as defined below;

$R_7$ is chosen from a hydrogen atom; a ($C_1$–$C_6$)alkyl radical; a monohydroxy($C_1$–$C_6$)alkyl radical: a polyhydroxy($C_2$–$C_6$)alkyl radical; a Z group as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a trifluoro($C_1$–$C_6$)alkyl radical; an aminosulphonyl($C_1$–$C_6$)alkyl radical; an N—Z-aminosulphonyl($C_1$–$C_6$)alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical, a ($C_1$–$C_6$) alkylcarbonyl($C_1$–$C_6$)alkyl radical; an amino($C_1$–$C_6$) alkyl radical, wherein the alkyl is unsubstituted or substituted by one or more hydroxyl radicals; and an amino($C_1$–$C_6$)alkyl radical, wherein the alkyl is unsubstituted or substituted by one or more hydroxyl radicals and the amine is substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$)alkylcarbonyl, ($C_1$–$C_6$) alkylcarboxyl, carbamyl, N—($C_1$–$C_6$)alkylcarbamyl, N,N-di($C_1$–$C_6$)alkylcarbamyl, thiocarbamyl and ($C_1$–$C_6$)alkylsulphonyl radicals, and from a Z group as defined below;

Z is chosen from the unsaturated cationic groups of following formulae (II) and (III) and the saturated cationic groups of following formula (IV):

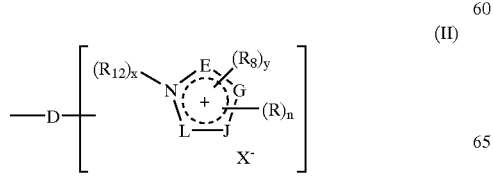
(II)

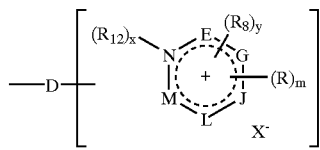
(III)

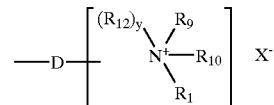
(IV)

wherein:

D is a linking arm which is a linear or branched alkyl chain which can be interrupted by one or more heteroatoms, can be substituted by one or more hydroxyl or ($C_1$–$C_6$)alkoxy radicals and can carry one or more ketone functional groups;

the E, G, J, L and M vertices, which are identical or different, are chosen from carbon, oxygen, sulphur and nitrogen atoms;

n is an integer ranging from 0 to 4;

m is an integer ranging from 0 to 5;

the R radicals, which are identical or different, are chosen from a second Z group identical to or different from the first Z group; a halogen atom; a hydroxyl radical; a ($C_1$–$C_6$)alkyl radical; a monohydroxy($C_1$–$C_6$)alkyl radical; a polyhydroxy ($C_2$–$C_6$)alkyl radical; a nitro radical; a cyano radical; a cyano($C_1$–$C_6$)alkyl radical; a ($C_1$–$C_6$)alkoxy radical; a tri($C_1$–$C_6$)alkylsilyl($C_1$–$C_6$)alkyl radical; an amido radical; a formyl radical; a carboxyl radical; a ($C_1$–$C_6$)alkylcarbonyl radical; a thio radical; a thio ($C_1$–$C_6$)alkyl radical; a ($C_1$–$C_6$)alkylthio radical; an amino radical; an amino radical protected by a ($C_1$–$C_6$)alkylcarbonyl, carbamyl or ($C_1$–$C_6$) alkylsulphonyl radical; an NHR" group and an NR"R'" group wherein R" and R'", which are identical or different, are chosen from a ($C_1$–$C_6$)alkyl radical, a monohydroxy($C_1$–$C_6$)alkyl radical and a polyhydroxy($C_2$–$C_6$)alkyl radical;

$R_8$ is chosen from a ($C_1$–$C_6$)alkyl radical; a monohydroxy($C_1$–$C_6$)alkyl radical; a polyhydroxy ($C_2$–$C_6$)alkyl radical; a cyano($C_1$–$C_6$)alkyl radical; a tri($C_1$–$C_6$)alkylsilyl($C_1$–$C_6$)alkyl radical; a ($C_1$–$C_6$) alkoxy($C_1$–$C_6$)alkyl radical; a carbamyl($C_1$–$C_6$) alkyl radical; a ($C_1$–$C_6$)alkylcarboxy($C_1$–$C_6$)alkyl radical; a benzyl radical; and a second Z group identical to or different from the first Z group;

$R_9$, $R_{10}$ and $R_{11}$, which are identical or different, are chosen from a ($C_1$–$C_6$)alkyl radical; a monohydroxy ($C_1$–$C_6$)alkyl radical; a polyhydroxy($C_2$–$C_6$)alkyl radical; a ($C_1$–$C_6$)alkoxy-($C_1$–$C_6$)alkyl radical; a cyano($C_1$–$C_6$)alkyl radical; an aryl radical; a benzyl radical; an amido($C_1$–$C_6$)alkyl radical; a tri($C_1$–$C_6$) alkylsilyl($C_1$–$C_6$)alkyl radical; and an amino($C_1$–$C_6$) alkyl radical, wherein the amine is protected by a ($C_1$–$C_6$)alkylcarbonyl, carbamyl or ($C_1$–$C_6$) alkylsulphonyl radical; or wherein two of the $R_9$, $R_{10}$ and $R_{11}$ radicals together form, with the nitrogen atom to which they are attached, a saturated carbonaceous 5- or 6-membered ring or a saturated 5- or 6-membered ring which can comprise one or more heteroatoms, wherein said ring is unsubstituted or substituted by a halogen atom, a hydroxyl radical, a ($C_1$–$C_6$)alkyl radical, a monohydroxy($C_1$–$C_6$)alkyl radical, a polyhydroxy($C_1$–$C_6$)alkyl radical, a nitro radical, a cyano radical, a cyano($C_1$–$C_6$)alkyl radical, a ($C_1$–$C_6$)alkoxy radical, a tri($C_1$–$C_6$)alkylsilyl($C_1$–$C_6$)alkyl radical, an amido radical, a formyl radical, a carboxyl radical, a keto($C_1$–$C_6$) alkyl radical, a thio radical, a thio($C_1$–$C_6$)alkyl radical, a ($C_1$–$C_6$)alkylthio radical, an amino radical or an amino radical protected by a ($C_1$–$C_6$) alkylcarbonyl, carbamyl or ($C_1$–$C_6$)alkylsulphonyl radical; or wherein one of the $R_9$, $R_{10}$ and $R_{11}$ radicals is a second Z group identical to or different from the first Z group:

$R_{12}$ is chosen from a ($C_1$–$C_6$)alkyl radical; a monohydroxy($C_1$–$C_6$)alkyl radical; a polyhydroxy($C_2$–$C_6$)alkyl radical; an aryl radical, a benzyl radical; an amino($C_1$–$C_6$)alkyl radical; an amino($C_1$–$C_6$) alkyl radical, wherein the amine is protected by a ($C_1$–$C_6$)alkylcarbonyl, carbamyl or ($C_1$–$C_6$) alkylsulphonyl radical; a carboxy($C_1$–$C_6$)alkyl radical; a cyano($C_1$–$C_6$)alkyl radical; a carbamyl-($C_1$–$C_6$)alkyl radical; a trifluoro($C_1$–$C_6$)alkyl radical; a tri($C_1$–$C_6$)alkylsilyl($C_1$–$C_6$)alkyl radical; a sulphonamido($C_1$–$C_6$)alkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N—($C_1$–$C_6$) alkylcarbamyl($C_1$–$C_6$)alkyl radical; and an N—($C_1$–$C_6$)alkylsulphonamido($C_1$–$C_6$)alkyl radical;

x and y are integers equal to 0 or 1, with the provisos that:

in the unsaturated cationic groups of formula (II):
when x=0, the D linking arm is attached to the nitrogen atom,
when x=1, the D linking arm is attached to one of the E, G, J or L vertices,
y can take the value 1 only when:
1) the E, G, J and L vertices are all carbon atoms and when the $R_8$ radical is carried by the nitrogen atom of the unsaturated ring; or
2) at least one of the E, G, J and L vertices is a nitrogen atom to which the $R_8$ radical is attached;

in the unsaturated cationic groups of formula (III):
when x=0, the D linking arm is attached to the nitrogen atom,
when x=1, the D linking arm is attached to one of the E, G, J, L or M vertices,
y can take the value 1 only when at least one of the E, G, J, L and M vertices is a divalent atom and when the $R_8$ radical is carried by the nitrogen atom of the unsaturated ring;

in the cationic groups of formula (IV):
when y=0, the D linking arm is attached to the nitrogen atom carrying the $R_9$, $R_{10}$ and $R_{11}$ radicals,
when y=1, two of the $R_9$, $R_{10}$ and $R_{11}$ radicals form, together with the nitrogen atom to which they are attached, a saturated carbonaceous 5- or 6-membered ring or a saturated 5- or 6-membered ring which can comprise one or more heteroatoms, wherein said ring is unsubstituted or substituted by a halogen atom, a hydroxyl radical, a ($C_1$–$C_6$)alkyl radical, a monohydroxy($C_1$–$C_6$)alkyl radical, a polyhydroxy($C_2$–$C_6$)alkyl radical, a nitro radical, a cyano radical, a cyano($C_1$–$C_6$)alkyl radical, a ($C_1$–$C_6$)alkoxy radical, a tri($C_1$–$C_6$) alkylsilyl($C_1$–$C_6$)alkyl radical, an amido radical, a formyl radical, a carboxyl radical, a keto($C_1$–$C_6$)alkyl radical, a thio radical, a thio ($C_1$–$C_6$)alkyl radical, a ($C_1$–$C_6$)alkylthio radical, an amino radical or an amino radical protected by a ($C_1$–$C_6$)alkylcarbonyl, carbamyl or ($C_1$–$C_6$)alkylsulphonyl radical; and the D linking arm is carried by a carbon atom of the said saturated ring;

$X^-$ is a monovalent or divalent anion;

with the provisos that:
in the compound of formula (I), at least one of $R_1$, $R_2$, $R_3$, $R_4$, $R_5$, and $R_6$ comprises at least one unsaturated cationic group Z of formula (II) wherein at least one of the E, G, J and L vertices is a nitrogen atom, and
when only one of the $R_1$, $R_2$, $R_3$, $R_4$ or $R_7$ radicals is a Z group wherein the D linking arm is an alkyl chain comprising a ketone functional group, then said ketone functional group is not directly attached to the nitrogen atom of the $NR_1R_2$ or $NR_3R_4$ group or to the oxygen atom of the $OR_7$ group when $R_5$ or $R_6$ is $OR_7$.

2. A compound according to claim 1, wherein D is a linear or branched alkyl chain comprising from 1 to 14 carbon atoms.

3. A compound according to claim 1, wherein D is a linear or branched alkyl chain which is interrupted by one or more heteroatoms chosen from oxygen, sulphur and nitrogen atoms.

4. A compound according to claim 1, wherein Z is an unsaturated cationic group of formula (II), and further wherein the ring of said formula (II) is chosen from pyrrole, imidazole, pyrazole, oxazole, thiazole and triazole rings.

5. A compound according to claim 1, wherein Z is an unsaturated cationic group of formula (III), and further wherein the ring of said formula (III) is chosen from pyridine, pyrimidine, pyrazine, oxazine and triazine rings.

6. A compound according to claim 1, wherein two of the $R_9$, $R_{10}$ and $R_{11}$ radicals in formula (IV) together form, with the nitrogen atom to which they are attached, a pyrrolidine ring, a piperidine ring, a piperazine ring or a morpholine ring, wherein said ring is unsubstituted or substituted by a halogen atom, a hydroxyl radical, a ($C_1$–$C_6$)alkyl radical, a monohydroxy($C_1$–$C_6$)alkyl radical, a polyhydroxy($C_2$–$C_6$) alkyl radical, a nitro radical, a cyano radical, a cyano($C_1$–$C_6$) alkyl radical, a ($C_1$–$C_6$)alkoxy radical, a tri($C_1$–$C_6$)alkylsilyl ($C_1$–$C_6$)alkyl radical, an amido radical, a formyl radical, a carboxyl radical, a ($C_1$–$C_6$)alkylcarbonyl radical, a thio radical, a thio($C_1$–$C_8$)alkyl radical, a ($C_1$–$C_6$)alkylthio radical, an amino radical or an amino radical protected by a ($C_1$–$C_6$)alkylcarbonyl, carbamyl or ($C_1$–$C_6$)alkylsulphonyl radical.

7. A compound according to claim 1, wherein $X^-$ is chosen from a halogen atom, a hydroxide, a hydrogen sulphate and a ($C_1$–$C_6$)alkyl sulphate.

8. A compound according to claim 1, wherein said cationic monobenzene nitrophenylenediamine is chosen from those of following formulae $(I)_1$ to $(I)_{15}$:

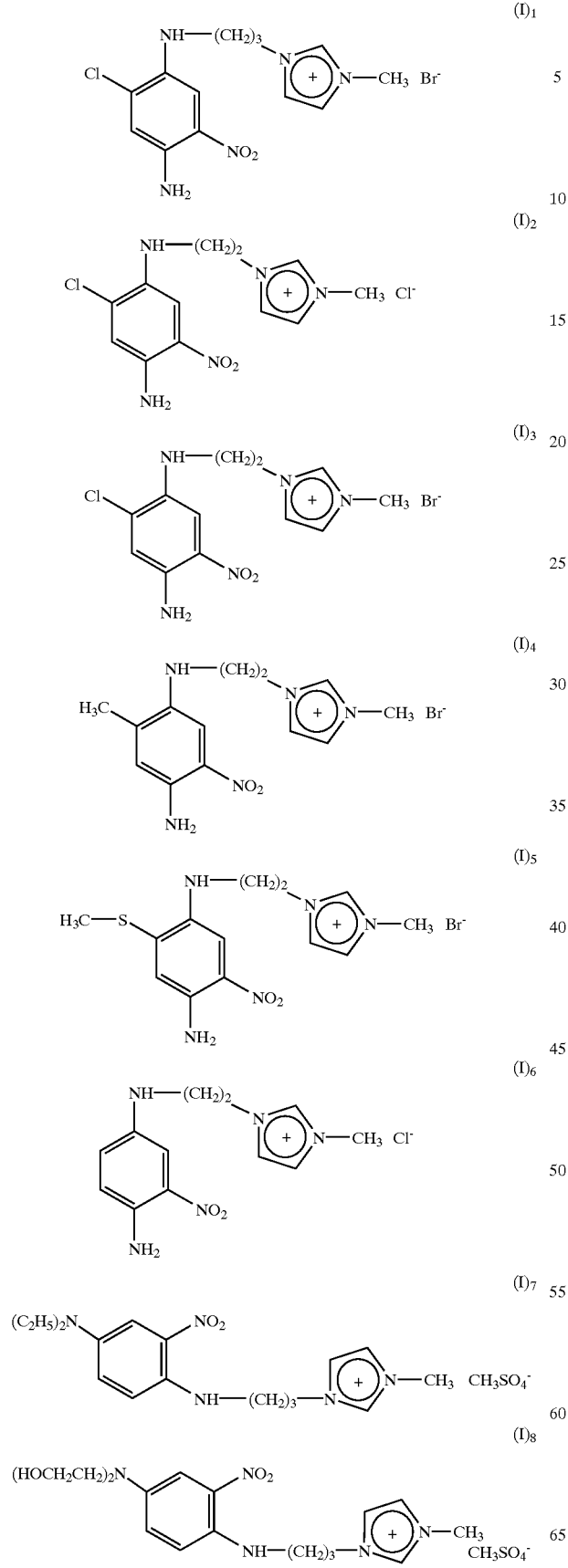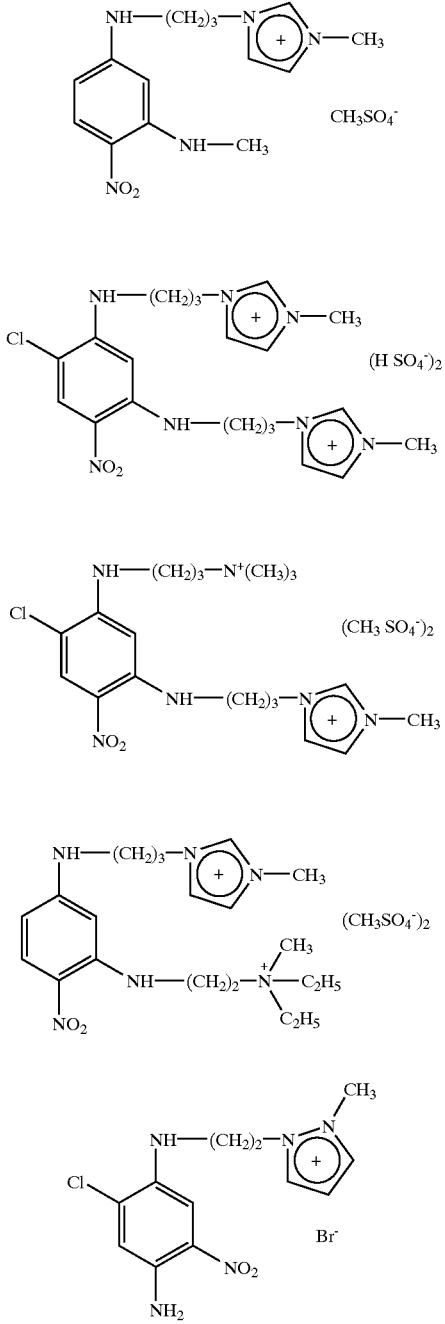

-continued

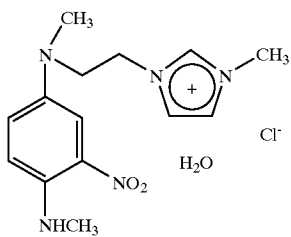

(I)15

9. A compound according to claim 1, wherein said acid addition salts are chosen from hydrochlorides, hydrobromides, sulphates, citrates, succinates, tartrates, lactates and acetates.

10. A dyeing composition for keratinous substances, comprising, in a medium appropriate for dyeing, at least one cationic monobenzene nitrophenylenediamine of following formula (I) or the acid addition salts thereof, said at least one cationic monobenzene nitrophenyldiamine being present in said composition in an amount effective for direct dyeing of keratinous substances:

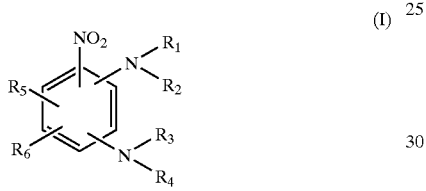

wherein:

$R_1$, $R_2$, $R_3$ and $R_4$, which can be identical or different, are chosen from a hydrogen atom; a Z group as defined below; a $(C_1-C_6)$alkyl radical; a mono-hydroxy $(C_1-C_6)$alkyl radical; a polyhydroxy$(C_2-C_6)$alkyl radical; a $(C_1-C_6)$alkoxy$(C_1-C_6)$alkyl radical; an aryl radical; a benzyl radical; a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$ alkylcarbamyl$(C_1C_6)$alkyl radical; a thiocarbamyl $(C_1-C_6)$alkyl radical; a trifluoro$(C_1-C_6)$alkyl radical; a sulpho$(C_1-C_6)$alkyl radical; a $(C_1-C_6)$alkylcarboxy $(C_1-C_6)$alkyl radical; a $(C_1-C_6)$alkylsulphinyl$(C_1-C_6)$ alkyl radical; an aminosulphonyl$(C_1-C_6)$alkyl radical; an N—Z-aminosulphonyl$(C_1-C_6)$alkyl radical; an N—$(C_1-C_6)$alkylaminosulphonyl$(C_1-C_6)$alkyl radical; an N,N-di$(C_1-C_6)$alkylaminosulphonyl$(C_1-C_6)$alkyl radical: a $(C_1-C_6)$alkylcarbonyl$(C_1-C_6)$alkyl radical; an amino$(C_1-C_6)$alkyl radical, wherein the alkyl is unsubstituted or substituted by one or more hydroxyl radicals; and an amino$(C_1-C_6)$alkyl radical, wherein the alkyl is unsubstituted or substituted by one or more hydroxyl radicals and the amine is substituted by one or two identical or different radicals which may together form, with the nitrogen atom to which they are respectively attached, a carbonaceous 5- or 6-membered ring or a 5- or 6-membered ring comprising one or more heteroatoms, or which are chosen from alkyl, monohydroxy$(C_1-C_6)$alkyl, polyhydroxy$(C_2-C_6)$alkyl, $(C_1-C_6)$alkylcarbonyl, carbamyl, N—$(C_1-C_6)$ alkylcarbamyl or N,N-di$(C_1-C_6)$alkylcarbamyl, $(Cl_1-C_6)$alkylsulphonyl, formyl, trifluoro$(C_1-C_6)$ alkylcarbonyl, $(C_1-C_6)$alkylcarboxyl and thiocarbamyl radicals, and from a Z group as defined below;

$R_5$ and $R_6$, which can be identical or different, are chosen from a hydrogen atom; a halogen atom; a Z group as defined below; a $(C_1-C_6)$alkylcarbonyl radical; an amino$(C_1-C_6)$alkylcarbonyl radical; an N—Z-amino $(C_1-C_6)$alkylcarbonyl radical; an N—$(C_1-C_6)$ alkylamino$(C_1-C_6)$alkylcarbonyl radical; an N,N-di $(C_1-C_6)$alkylamino$(C_1-C_6)$alkylcarbonyl radical; an amino$(C_1-C_6)$alkylcarbonyl$(C_1-C_6)$alkyl radical; an N—Z-amino$(C_1-C_6)$alkylcarbonyl$(C_1-C_6)$alkyl radical; an N—$(C_1-C_6)$alkylamino$(C_1-C_6)$alkylcarbonyl $(C_1-C_6)$alkyl radical; an N,N-di$(C_1-C_6)$alkylamino $(C_1-C_6)$alkylcarbonyl$(C_1-C_6)$alkyl radical; a carboxyl radical; a $(C_1-C_6)$alkylcarboxyl radical; a $(C_1-C_6)$ alkylsulphonyl radical; an aminosulphonyl radical; an N—Z-aminosulphonyl radical; an N—$(C_1-C_6)$ alkylaminosulphonyl radical; an N,N-di$(C_1-C_6)$ alkylaminosulphonyl radical; an aminosulphonyl $(C_1-C_6)$alkyl radical; an N—Z-aminosulphonyl $(C_1-C_6)$alkyl radical; an N—$(C_1-C_6)$ alkylaminosulphonyl$(C_1-C_6)$alkyl radical, an N,N-di $(C_1-C_6)$alkylaminosulphonyl$(C_1-C_6)$alkyl radical; a carbamyl radical; an N—$(C_1-C_6)$alkylcarbamyl radical; an N,N-di$(C_1-C_6)$alkylcarbamyl radical; a carbamyl$(C_1-C_6)$alkyl radical; an N—$(C_1-C_6)$ alkylcarbamyl$(C_1-C_6)$alkyl radical; an N,N-di$(C_1-C_6)$ alkylcarbamyl$(C_1-C_6)$alkyl radical; a $(C_1-C_6)$alkyl radical; a monohydroxy$(C_1-C_6)$alkyl radical; a polyhydroxy$(C_2C_6)$alkyl radical; a $(C_1-C_6)$alkoxy $(C_1-C_6)$alkyl radical; a trifluoro$(C_1-C_6)$alkyl radical; a cyano radical; an $OR_7$ or —$SR_7$ group wherein $R_7$ is as defined below; and an amino$(C_1-C_6)$alkyl radical, wherein the alkyl is unsubstituted or substituted by one or more hydroxyl radicals and the amine is unsubstituted or substituted by one or two identical or different radicals which may together form, with the nitrogen atom to which they are attached, a carbonaceous 5- or 6-membered ring or a 5- or 6-membered ring comprising one or more heteroatoms, or which are chosen from $(C_1-C_6)$alkyl, monohydroxy$(C_1-C_6)$alkyl, polyhydroxy$(C_1-C_6)$alkyl, $(C_1-C_6)$alkylcarbonyl, carbamyl, N—$(C_1-C_6)$alkylcarbamyl, N,N-di$(C_1-C_6)$ alkylcarbamyl, $(C_1-C_6)$alkylsulphonyl, formyl, trifluoro$(C_1-C_6)$alkylcarbonyl, $(C_1-C_6)$alkylcarboxyl and thiocarbamyl radicals, and from a Z group as defined below;

$R_7$ is chosen from a hydrogen atom; a $(C_1-C_6)$alkyl radical; a monohydroxy$(C_1-C_6)$alkyl radical; a polyhydroxy$(C_2-C_6)$alkyl radical; a Z group as defined below; a $(C_1-C_6)$alkoxy$(C_1-C_6)$alkyl radical; an aryl radical; a benzyl radical; a carboxy$(C_1-C_6)$alkyl radical; a $(C_1-C_6)$alkyl radical; a cyano$(C_1-C_6)$alkyl radical; a carbamyl$(C_1-C_6)$alkyl radical; an N—$(C_1-C_6)$ alkylcarbamyl$(C_1-C_6)$alkyl radical; an N,N-di$(C_1-C_6)$ alkylcarbamyl$(C_1-C_6)$alkyl radical; a trifluoro$(C_1-C_6)$ alkyl radical; an aminosulphonyl$(C_1-C_6)$alkyl radical; an N—Z-aminosulphonyl$(C_1-C_6)$alkyl radical; an N—$(C_1-C_6)$alkylaminosulphonyl$(C_1-C_6)$alkyl radical; an N,N-di$(C_1-C_6)$alkylaminosulphonyl$(C_1-C_6)$alkyl radical; a $(C_1-C_6)$alkylsulphinyl$(C_1-C_6)$alkyl radical; a $(C_1-C_6)$alkylsulphonyl$(C_1-C_6)$alkyl radical; a $(C_1-C_6)$ alkylcarbonyl$(C_1-C_6)$alkyl radical; an amino$(C_1-C_6)$ alkyl radical, wherein the alkyl is unsubstituted or substituted by one or more hydroxyl radicals; and an amino$(C_1-C_6)$alkyl radical, wherein the alkyl is unsubstituted or substituted by one or more hydroxyl radicals and the amine is substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$)alkylcarbonyl, ($C_1$–$C_6$)alkylcarboxyl, carbamyl, N—($C_1$–$C_6$)alkylcarbamyl, N,N-di($C_1$–$C_6$)alkylcarbamyl, thiocarbamyl and ($C_1$–$C_6$)alkylsulphonyl radicals, and from a Z group as defined below;

Z is chosen from the unsaturated cationic groups of following formulae (II) and (III) and the saturated cationic groups of following formula (IV):

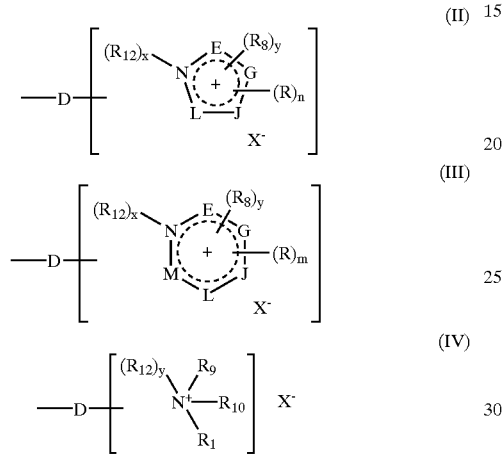

wherein:

D is a linking arm which is a linear or branched alkyl chain which can be interrupted by one or more heteroatoms, can be substituted by one or more hydroxyl or ($C_1$–$C_6$)alkoxy radicals and can carry one or more ketone functional groups;

the E, G, J, L and M vertices, which are identical or different, are chosen from carbon, oxygen, sulphur and nitrogen atoms;

n is an integer ranging from 0 to 4:

m is an integer ranging from 0 to 5;

the R radicals, which are identical or different, are chosen from a second Z group identical to or different from the first Z group; a halogen atom; a hydroxyl radical; a ($C_1$–$C_6$)alkyl radical; a monohydroxy($C_1$–$C_6$)alkyl radical; a polyhydroxy($C_2$–$C_6$)alkyl radical; a nitro radical; a cyano radical; a cyano($C_1$–$C_6$)alkyl radical; a ($C_1$–$C_6$)alkoxy radical; a tri($C_1$–$C_6$)alkylsilyl($C_1$–$C_6$)alkyl radical; an amido radical; a formyl radical; a carboxyl radical; a ($C_1$–$C_6$)alkylcarbonyl radical; a thio radical; a thio($C_1$–$C_6$)alkyl radical; a ($C_1$–$C_6$)alkylthio radical; an amino radical; an amino radical protected by a ($C_1$–$C_6$)alkylcarbonyl, carbamyl or ($C_1$–$C_6$)alkylsulphonyl radical, an NHR" group and an NR"R'" group wherein R" and R'", which are identical or different, are chosen from a ($C_1$–$C_6$)alkyl radical, a monohydroxy($C_1$–$C_6$)alkyl radical and a polyhydroxy($C_2$–$C_6$)alkyl radical;

$R_8$ is chosen from a ($C_1$–$C_6$)alkyl radical; a monohydroxy($C_1$–$C_6$)alkyl radical; a polyhydroxy($C_2$–$C_6$)alkyl radical; a cyano($C_1$–$C_6$)alkyl radical; a tri($C_1$–$C_{14}$)alkylsilyl($C_1$–$C_6$)alkyl radical; a ($C_1$–$C_6$)alkoxy($C_1$–$C_6$)alkyl radical; a carbamyl($C_1$–$C_6$)alkyl radical; a ($C_1$–$C_6$)alkylcarboxy($C_1$–$C_6$)alkyl radical; a benzyl radical; and a second Z group identical to or different from the first Z group;

$R_9$, $R_{10}$ and $R_{11}$, which are identical or different, are chosen from a ($C_1$–$C_6$)alkyl radical; a monohydroxy($C_1$–$C_6$)alkyl radical; a polyhydroxy($C_2$–$C_6$)alkyl radical; a ($C_1$–$C_6$)alkoxy-($C_1$–$C_6$)alkyl radical; a cyano($C_1$–$C_6$)alkyl radical; an aryl radical; a benzyl radical; an amido($C_1$–$C_6$)alkyl radical; a tri($C_1$–$C_6$)alkylsilyl($C_1$–$C_6$)alkyl radical; and an amino($C_1$–$C_6$)alkyl radical, wherein the amine is protected by a ($C_1$–$C_6$)alkylcarbonyl, carbamyl or ($C_1$–$C_6$)alkylsulphonyl radical; or wherein two of the $R_9$, $R_{10}$ and $R_{11}$ radicals together form, with the nitrogen atom to which they are attached, a saturated carbonaceous 5- or 6-membered ring or a saturated 5- or 6-membered ring which can comprise one or more heteroatoms, wherein said ring is unsubstituted or substituted by a halogen atom, a hydroxyl radical, a ($C_1$–$C_6$)alkyl radical, a monohydroxy($C_1$–$C_6$)alkyl radical, a polyhydroxy($C_2$–$C_6$)alkyl radical, a nitro radical, a cyano radical, a cyano($C_1$–$C_6$)alkyl radical, a ($C_1$–$C_6$)alkoxy radical, a tri($C_1$–$C_6$)alkylsilyl($C_1$–$C_6$)alkyl radical, an amido radical, a formyl radical, a carboxyl radical, a keto($C_1$–$C_6$)alkyl radical, a thio radical, a thio($C_1$–$C_6$)alkyl radical, a ($C_1$–$C_6$)alkylthio radical, an amino radical or an amino radical protected by a ($C_1$–$C_6$)alkylcarbonyl, carbamyl or ($C_1$–$C_6$)alkylsulphonyl radical; or wherein one of the $R_9$, $R_{10}$ and $R_{11}$ radicals is a second Z group identical to or different from the first Z group;

$R_{12}$ is chosen from a ($C_1$–$C_6$)alkyl radical; a monohydroxy($C_1$–$C_6$)alkyl radical; a polyhydroxy($C_2$–$C_6$)alkyl radical; an aryl radical; a benzyl radical; an amino($C_1$–$C_6$)alkyl radical; an amino($C_1$–$C_6$)alkyl radical, wherein the amine is protected by a ($C_1$–$C_6$)alkylcarbonyl, carbamyl or ($C_1$–$C_6$)alkylsulphonyl radical; a carboxy($C_1$–$C_6$)alkyl radical; a cyano($C_1$–$C_6$)alkyl radical; a carbamyl-($C_1$–$C_6$)alkyl radical; a trifluoro($C_1$–$C_6$)alkyl radical; a tri($C_1$–$C_6$)alkylsilyl($C_1$–$C_6$)alkyl radical; a sulphonamido($C_1$–$C_6$)alkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; and an N—($C_1$–$C_6$)alkylsulphonamido($C_1$–$C_6$)alkyl radical;

x and y are integers equal to 0 or 1, with the provisos that:

in the unsaturated cationic groups of formula (II):
when x=0, the D linking arm is attached to the nitrogen atom,
when x=1, the D linking arm is attached to one of the E, G, J or L vertices,
y can take the value 1 only when:
1) the E, G, J and L vertices are all carbon atoms and when the $R_8$ radical is carried by the nitrogen atom of the unsaturated ring; or
2) at least one of the E, G, J and L vertices is a nitrogen atom to which the $R_8$ radical is attached;

in the unsaturated cationic groups of formula (III):
when x=0, the D linking arm is attached to the nitrogen atom, when x=1, the D linking arm is attached to one of the E, G, J, L or M vertices, y can take the value 1 only when at least one of the E, G, J, L and M vertices is a divalent atom and when the $R_8$ radical is carried by the nitrogen atom of the unsaturated ring;

in the cationic groups of formula (IV):

when y=0, the D linking arm is attached to the nitrogen atom carrying the $R_9$, $R_{10}$ and $R_{11}$ radicals, when y=1, two of the $R_9$, $R_{10}$ and $R_{11}$ radicals form, together with the nitrogen atom to which they are attached, a saturated carbonaceous 5- or 6-membered ring or a saturated 5- or 6-membered ring which can comprise one or more heteroatoms, wherein said ring is unsubstituted or substituted by a halogen atom, a hydroxyl radical, a $(C_1-Ce)$alkyl radical, a monohydroxy$(C_1-C_6)$alkyl radical, a polyhydroxy$(C_1-C_6)$alkyl radical, a nitro radical, a cyano radical, a cyano$(C_1-C_6)$alkyl radical, a $(C_1-C_6)$alkoxy radical, a tri$(C_1-C_6)$alkylsilyl$(C_1-C_6)$alkyl radical, an amido radical, a formyl radical, a carboxyl radical, a keto$(C_1-C_6)$alkyl radical, a thio radical, a thio $(C_1-C_6)$alkyl radical, a $(C_1-C_6)$alkylthio radical, an amino radical or an amino radical protected by a $(C_1-C_6)$alkylcarbonyl, carbamyl or $(C_1-C_6)$alkylsulphonyl radical; and the D linking arm is c arded by a carbon atom of the said saturated ring;

X⁻ is a monovalent or divalent anion;

with the provisos that:

in the compound of formula (I), at least one of $R_1$, $R_2$, $R_3$, $R_4$, $R_5$, and $R_6$ comprises at least one unsaturated cationic group Z of formula (II) wherein at least one of the E, G, J and L vertices is a nitrogen atom, and when only one of the $R_1$, $R_2$, $R_3$, $R_4$ or $R_7$ radicals is a Z group wherein the D linking arm is an alkyl chain comprising a ketone functional group, then said ketone functional group is not directly attached to the nitrogen atom of the $NR_1R_2$ or $NR_3R_4$ group or to the oxygen atom of the $OR_7$ group when $R_5$ or $R_6$ is $OR_7$.

11. A composition according to claim 10, wherein said keratinous substances are human keratinous fibers.

12. A composition according to claim 11, wherein said human keratinous fibers are hair.

13. A composition according to claim 10, wherein said composition has a pH ranging from 3 to 12.

14. A composition according to claim 10, wherein said at least one cationic monobenzene nitrophenylenediamine is present in an amount ranging from 0.005 to 12% by weight with respect to the total weight of the composition.

15. A composition according to claim 14, wherein said at least one cationic monobenzene nitrophenylenediamine is present in an amount ranging from 0.05 to 6% by weight with respect to the total weight of the composition.

16. A composition according to claim 10, wherein said composition comprises other direct dyes chosen from nitrobenzene dyes other than said at least one cationic monobenzene nitrophenylenediamine of formula (I).

17. A composition according to claim 16, wherein said other direct dyes are chosen from nitrodiphenylamines, nitroanilines, nitrophenol ethers or nitrophenols, nitropyridines, anthraquinone dyes, mono- or diazo-dyes, triarylmethane, azine, acridine or xanthene dyes and metal complex dyes.

18. A composition according to claim 10, wherein said medium appropriate for dyeing is an aqueous medium comprising water and/or organic solvents chosen from alcohols, glycols and glycol ethers, said medium being present in said composition in an amount ranging from 1 to 40% by weight with respect to the total weight of the composition.

19. A process for dyeing keratinous fibers by direct coloring, comprising applying a dyeing composition to dry or wet keratinous fibers, said dyeing composition comprising, in a medium appropriate for dyeing, at least one cationic monobenzene nitrophenylenediamine of following formula (I) or the acid addition salts thereof, said at least one cationic monobenzene nitroaniline being present in said composition in an amount effective for direct dyeing of keratinous fibers:

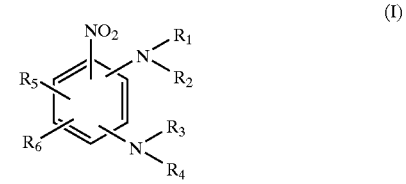

wherein:

$R_1$, $R_2$, $R_3$ and $R_4$, which can be identical or different, are chosen from a hydrogen atom; a Z group as defined below; a $(C_1-C_6)$alkyl radical; a mono-hydroxy $(C_1-C_6)$alkyl radical; a polyhydroxy$(C_2-C_6)$alkyl radical; a $(C_1-C_6)$alkoxy$(C_1-C_6)$alkyl radical; an aryl radical; a benzyl radical: a cyano$(C_1-C_6)$alkyl radical; a carbamyl$(C_1-C_6)$alkyl radical; an N—$(C_1-C_6)$alkylcarbamyl$(C_1-C_6)$alkyl radical; an N,N-di$(C_1-C_6)$alkylcarbamyl$(C_1-C_6)$alkyl radical; a thiocarbamyl $(C_1-C_6)$alkyl radical; a trifluoro$(C_1-C_6)$alkyl radical; a sulpho$(C_1-C_6)$alkyl radical; a $(C_1-C_6)$alkylcarboxy $(C_1-C_6)$alkyl radical; a $(C_1-C_6)$alkylsulphinyl$(C_1-C_6)$ alkyl radical; an aminosulphonyl$(C_1-C_6)$alkyl radical; an N—Z-aminosulphonyl$(C_1-C_6)$alkyl radical: an N—$(C_1-C_6)$alkylaminosulphonyl$(C_1-C_6)$alkyl radical; an N,N-di$(C_1-C_6)$alkylaminosulphonyl$(C_1-C_6)$alkyl radical; a $(C_1-C_6)$alkylcarbonyl$(C_1-C_6)$alkyl radical; an amino$(C_1-C_6)$alkyl radical, wherein the alkyl is unsubstituted or substituted by one or more hydroxyl radicals; and an amino$(C_1-C_6)$alkyl radical, wherein the alkyl is unsubstituted or substituted by one or more hydroxyl radicals and the amine is substituted by one or two identical or different radicals which may together form, with the nitrogen atom to which they are respectively attached, a carbonaceous 5- or 6-membered ring or a 5- or 6-membered ring comprising one or more heteroatoms, or which are chosen from alkyl, monohydroxy$(C_1-C_6)$alkyl, polyhydroxy$(C_2-C_6)$alkyl, $(C_1-C_6)$alkylcarbonyl, carbamyl, N—$(C_1-C_6)$ alkylcarbamyl or N,N-di$(C_1-C_6)$alkylcarbamyl, $(C_1-C_6)$alkylsulphonyl, formyl, trifluoro$(C_1-C_6)$ alkylcarbonyl, $(C_1-C_6)$alkylcarboxyl and thiocarbamyl radicals, and from a Z group as defined below;

$R_5$ and $R_6$, which can be identical or different, are chosen from a hydrogen atom; a halogen atom; a Z group as defined below; a $(C_1-C_6)$alkylcarbonyl radical; an amino$(C_1-C_6)$alkylcarbonyl radical; an N—Z-amino $(C_1-C_6)$alkylcarbonyl radical; an N—$(C_1-C_6)$ alkylamino$(C_1-C_6)$alkylcarbonyl radical; an N,N-di $(C_1-C_6)$alkylamino$(C_1-C_6)$alkylcarbonyl radical; an amino$(C_1-C_6)$alkylcarbonyl$(C_1-C_6)$alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl ($C_1$–$C_6$)alkyl radical; an N,N-di($C_1$–$C_6$)alkylamino ($C_1$–$C_6$)alkylcarbonyl($C_1$–$C_6$)alkyl radical; a carboxyl radical; a ($C_1$–$C_6$)alkylcarboxyl radical; a ($C_1$–$C_6$) alkylsulphonyl radical; an aminosulphonyl radical; an N—Z-aminosulphonyl radical; an N—($C_1$–$C_6$) alkylaminosulphonyl radical; an N,N-di($C_1$–$C_6$) alkylaminosulphonyl radical; an aminosulphonyl ($C_1$–$C_6$)alkyl radical; an N—Z-aminosulphonyl ($C_1$–$C_6$)alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a ($C_1$–$C_6$)alkyl radical; a monohydroxy($C_1$–$C_6$)alkyl radical; a polyhydroxy($C_2$–$C_6$)alkyl radical; a ($C_1$–$C_6$)alkoxy ($C_1$–$C_6$)alkyl radical; a trifluoro($C_1$–$C_6$)alkyl radical; a cyano radical; an $OR_7$ or —$SR_7$ group wherein $R_7$ is as defined below; and an amino($C_1$–$C_6$)alkyl radical, wherein the alkyl is unsubstituted or substituted by one or more hydroxyl radicals and the amine is unsubstituted or substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_1$–$C_6$,)alkyl, ($C_1$–$C_6$)alkylcarbonyl, carbamyl, N—($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, and from a Z group as defined below;

$R_7$ is chosen from a hydrogen atom; a ($C_1$–$C_6$)alkyl radical; a monohydroxy($C_1$–$C_6$)alkyl radical; a polyhydroxy($C_1$–$C_6$)alkyl radical; a Z group as defined below; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy($C_1$–$C_6$)alkyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a trifluoro($C_1$–$C_6$)alkyl radical; an aminosulphonyl($C_1$–$C_6$)alkyl radical; an N—Z-aminosulphonyl($C_1$–$C_6$)alkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$) alkylsulphonyl($C_1$–$C_6$)alkyl radical; a ($C_1$–$C_6$) alkylcarbonyl($C_1$–$C_6$)alkyl radical; an amino($C_1$–$C_6$) alkyl radical, wherein the alkyl is unsubstituted or substituted by one or more hydroxyl radicals; and an amino($C_1$–$C_6$)alkyl radical, wherein the alkyl is unsubstituted or substituted by one or more hydroxyl radicals and the amine is substituted by one or two identical or different radicals which may together form, with the nitrogen atom to which they are attached, a carbonaceous 5- or 6-membered ring or a 5- or 6-membered ring comprising one or more heteroatoms, or which are chosen from ($C_1$–$C_6$)alkyl, monohydroxy($C_1$–$C_6$)alkyl, polyhydroxy($C_2$–$C_6$)alkyl, ($C_1$–$C_6$)alkylcarbonyl, formyl, trifluoro($C_1$–$C_6$)alkylcarbonyl, ($C_1$–$C_6$) alkylcarboxyl, carbamyl, N—($C_1$–$C_6$)alkylcarbamyl, N,N-di($C_1$–$C_6$)alkylcarbamyl, thiocarbamyl and ($C_1$–$C_6$)alkylsulphonyl radicals, and from a Z group as defined below;

Z is chosen from the unsaturated cationic groups of following formulae (II) and (III) and the saturated cationic groups of following formula (IV):

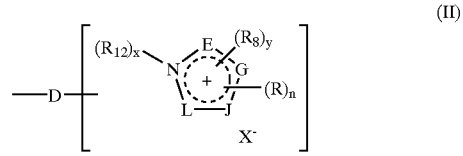

(II)

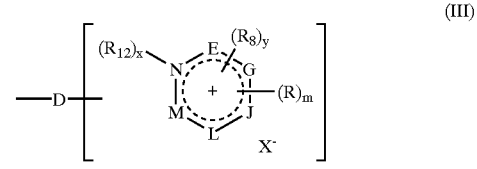

(III)

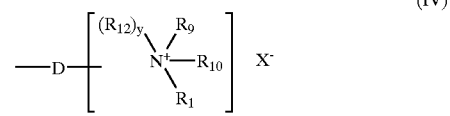

(IV)

wherein:

D is a linking arm which is a linear or branched alkyl chain which can be interrupted by one or more heteroatoms, can be substituted by one or more hydroxyl or ($C_1$–$C_6$)alkoxy radicals and can carry one or more ketone functional groups;

the E, G, J, L and M vertices, which are identical or different, are chosen from carbon, oxygen, sulphur and nitrogen atoms;

n is an integer ranging from 0 to 4;

m is an integer ranging from 0 to 5;

the R radicals, which are identical or different, are chosen from a second Z group identical to or different from the first Z group; a halogen atom; a hydroxyl radical; a ($C_1$–$C_6$)alkyl radical; a monohydroxy($C_1$–$C_6$)alkyl radical; a polyhydroxy ($C_2$–$C_6$)alkyl radical; a nitro radical; a cyano radical; a cyano($C_1$–$C_6$)alkyl radical; a ($C_1$–$C_6$)alkoxy radical; a tri($C_1$–$C_6$)alkylsilyl($C_1$–$C_6$)alkyl radical; an amido radical; a formyl radical; a carboxyl radical; a ($C_1$–$C_6$)alkylcarbonyl radical; a thio radical; a thio ($C_1$–$C_6$)alkyl radical; a ($C_1$–$C_6$)alkylthio radical; an amino radical; an amino radical protected by a ($C_1$–$C_6$)alkylcarbonyl, carbamyl or ($C_1$–$C_6$) alkylsulphonyl radical; an NHR" group and an NR"R"' group wherein R" and R"', which are identical or different, are chosen from a ($C_1$–$C_6$)alkyl radical, a monohydroxy($C_1$–$C_6$)alkyl radical and a polyhydroxy($C_1$–$C_6$)alkyl radical;

$R_8$ is chosen from a ($C_1$–$C_6$)alkyl radical; a monohydroxy($C_1$–$C_6$)alkyl radical; a polyhydroxy ($C_2$–$C_6$)alkyl radical; a cyano($C_1$–$C_6$)alkyl radical; a tri($C_1$–$C_6$)alkylsilyl($C_1$–$C_6$)alkyl radical; a ($C_1$–$C_6$) alkoxy($C_1$–$C_6$)alkyl radical; a carbamyl($C_1$–$C_6$) alkyl radical; a ($C_1$–$C_6$)alkylcarboxy($C_1$–$C_6$)alkyl radical; a benzyl radical; and a second Z group identical to or different from the first Z group;

$R_9$, $R_{10}$ and $R_{11}$, which are identical or different, are chosen from a ($C_1$–$C_6$)alkyl radical; a monohydroxy ($C_1$–$C_6$)alkyl radical; a polyhydroxy($C_2$–$C_6$)alkyl radical; a ($C_1$–$C_6$)alkoxy-($C_1$–$C_6$)alkyl radical; a cyano($C_1$–$C_6$)alkyl radical; an aryl radical; a benzyl radical; an amido($C_1$–$C_6$)alkyl radical; a tri($C_1$–$C_6$)alkylsilyl($C_1$–$C_6$)alkyl radical; and an amino($C_1$–$C_6$)alkyl radical, wherein the amine is protected by a ($C_1$–$C_6$)alkylcarbonyl, carbamyl or ($C_1$–$C_6$)alkylsulphonyl radical; or wherein two of the $R_9$, $R_{10}$ and $R_{11}$ radicals together form, with the nitrogen atom to which they are attached, a saturated carbonaceous 5- or 6-membered ring or a saturated 5- or 6-membered ring which can comprise one or more heteroatoms, wherein said ring is unsubstituted or substituted by a halogen atom, a hydroxyl radical, a ($C_1$–$C_6$)alkyl radical, a monohydroxy($C_1$–$C_6$)alkyl radical, a polyhydroxy($C_2$–$C_6$)alkyl radical, a nitro radical, a cyano radical, a cyano($C_1$–$C_6$)alkyl radical, a ($C_1$–$C_6$)alkoxy radical, a tri($C_1$–$C_6$)alkylsilyl($C_1$–$C_6$)alkyl radical, an amido radical, a formyl radical, a carboxyl radical, a keto($C_1$–$C_6$)alkyl radical, a thio radical, a thio($C_1$–$C_6$)alkyl radical, a ($C_1$–$C_6$)alkylthio radical, an amino radical or an amino radical protected by a ($C_1$–$C_6$)alkylcarbonyl, carbamyl or ($C_1$–$C_6$)alkylsulphonyl radical; or wherein one of the $R_9$, $R_{10}$ and $R_{11}$ radicals is a second Z group identical to or different from the first Z group;

$R_{12}$ is chosen from a ($C_1$–$C_6$)alkyl radical; a monohydroxy($C_1$–$C_6$)alkyl radical; a polyhydroxy($C_2$–$C_6$)alkyl radical; an aryl radical; a benzyl radical; an amino($C_1$–$C_6$)alkyl radical; an amino($C_1$–$C_6$)alkyl radical, wherein the amine is protected by a ($C_1$–$C_6$)alkylcarbonyl, carbamyl or ($C_1$–$C_6$)alkylsulphonyl radical; a carboxy($C_1$–$C_6$)alkyl radical; a cyano($C_1$–$C_6$)alkyl radical; a carbamyl-($C_1$–$C_6$)alkyl radical; a trifluoro($C_1$–$C_6$)alkyl radical; a tri($C_1$–$C_6$)alkylsilyl($C_1$–$C_6$)alkyl radical; a sulphonamido($C_1$–$C_6$)alkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylketo($C_1$–$C_6$)alkyl radical: an N—($C_1$–$C_6$)alkylcarbamyl($C_1$–$C_6$)alkyl radical; and an N—($C_1$–$C_6$)alkylsulphonamido($C_1$–$C_6$)alkyl radical;

x and y are integers equal to 0 or 1, with the provisos that:

in the unsaturated cationic groups of formula (II):
when x=0, the D linking arm is attached to the nitrogen atom,
when x 1, the D linking arm is attached to one of the E, G, J or L vertices,
y can take the value 1 only when:
1) the E, G, J and L vertices are all carbon atoms and when the $R_8$ radical is carried by the nitrogen atom of the unsaturated ring; or
2) at least one of the E, G, J and L vertices is a nitrogen atom to which the $R_8$ radical is attached;

in the unsaturated cationic groups of formula (III):
when x=0, the D linking arm is attached to the nitrogen atom, when x=1, the D linking arm is attached to one of the E, G, J, L or M vertices,
y can take the value 1 only when at least one of the E, G, J, L and M vertices is a divalent atom and when the $R_8$ radical is carried by the nitrogen atom of the unsaturated ring;

in the cationic groups of formula (IV):
when y=0, the D linking arm is attached to the nitrogen m carrying the $R_9$, $R_{10}$ and $R_{11}$ radicals,
when y=1, two of the $R_9$, $R_{10}$ and $R_{11}$ radicals form, together with the nitrogen atom to which they are attached, a saturated carbonaceous 5- or 6-membered ring or a saturated 5- or 6-membered ring which can comprise one or more heteroatoms, wherein said ring is unsubstituted or substituted by a halogen atom, a hydroxyl radical, a ($C_1$–$C_6$)alkyl radical, a monohydroxy($C_1$–$C_6$)alkyl radical, a polyhydroxy($C_2$–$C_6$)alkyl radical, a nitro radical, a cyano radical, a cyano($C_1$–$C_6$)alkyl radical, a ($C_1$–$C_6$)alkoxy radical, a tri($C_1$–$C_6$)alkylsilyl($C_1$–$C_6$)alkyl radical, an amido radical, a formyl radical, a carboxyl radical, a keto($C_1$–$C_6$)alkyl radical, a thio radical, a thio ($C_1$–$C_6$)alkyl radical, a ($C_1$–$C_6$)alkylthio radical, an amino radical or an amino radical protected by a ($C_1$–$C_6$)alkylcarbonyl, carbamyl or ($C_1$–$C_6$)alkylsulphonyl radical; and the D linking arm is carried by a carbon atom of the said saturated ring;

$X^-$ is a monovalent or divalent anion;

with the provisos that:
in the compound of formula (I), at least one of $R_1$, $R_2$, $R_3$, $R_4$, $R_5$, and $R_6$ comprises at least one unsaturated cationic group Z of formula (II) wherein at least one of the E, G, J and L vertices is a nitrogen atom, and
when only one of the $R_1$, $R_2$, $R_3$, $R_4$ or $R_7$ radicals is a Z group wherein the D linking arm is an alkyl chain comprising a ketone functional group, then said ketone functional group is not directly attached to the nitrogen atom of the $NR_1R_2$ or $NR_3R_4$ group or to the oxygen atom of the $OR_7$ group when $R_5$ or $R_6$ is $OR_7$.

20. A process according to claim 19, wherein said keratinous fibers are human keratinous fibers.

21. A process according to claim 20, wherein said human keratinous fibers are hair.

22. A process according to claim 19, wherein said dyeing composition is applied to dry or wet keratinous fibers and said fibers are dried without intermediate rinsing.

23. A process according to claim 19, wherein said dyeing composition is applied to dry or wet keratinous fibers and, after said composition is allowed to act on said fibers for an exposure time ranging from 3 to 60 minutes, said fibers are rinsed, optionally washed and again rinsed, and dried.

* * * * *

UNITED STATES PATENT AND TRADEMARK OFFICE
CERTIFICATE OF CORRECTION

PATENT NO. : 6,464,731 B1  
DATED : October 15, 2002  
INVENTOR(S) : Alain Genet and Alan Lagrange It is certified that error appears in the above-identified patent and that said Letters Patent is hereby corrected as shown below:

Column 24,  
In the structure of formula (I):

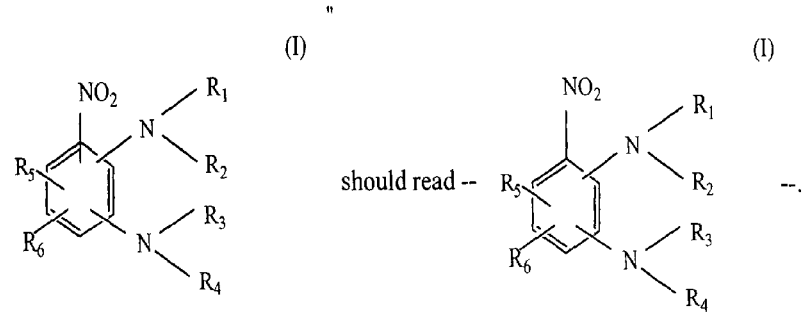

Lines 13-14, "mono-hydroxy($C_1$-$C_6$)alkyl" should read -- monohydroxy($C_1$-$C_6$)alkyl --.  
Lines 17-18, "N-($C_1$-$C_6$)alkylcarbamyl($C_1C_6$)alkyl" should read  
-- N-($C_1$-$C_6$)alkylcarbamyl($C_1$-$C_6$)alkyl --.  
Line 66, "radical:" should read -- radical; --.

Column 25,  
Line 24, "radical:" should read -- radical; --.  
Line 39, "radical," should read -- radical; --.

UNITED STATES PATENT AND TRADEMARK OFFICE
CERTIFICATE OF CORRECTION

PATENT NO. : 6,464,731 B1
DATED : October 15, 2002
INVENTOR(S) : Alain Genet and Alan Lagrange It is certified that error appears in the above-identified patent and that said Letters Patent is hereby corrected as shown below:

Column 26,
In the structure for formula (IV):

"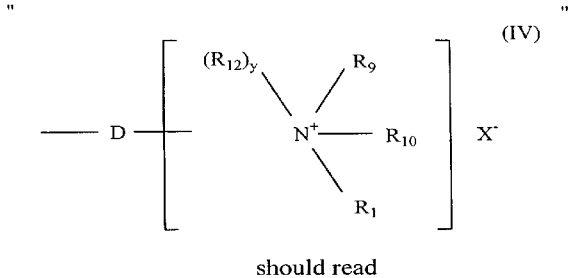"

should read

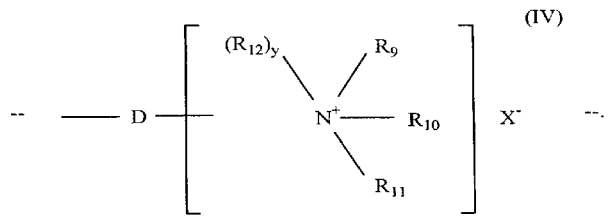 --.

Column 27,
Line 12, "group:" should read -- group; --.

Column 28,
Line 57, "thio($C_1$-$C_8$)alkyl" should read -- thio($C_1$-$C_6$)alkyl --.

UNITED STATES PATENT AND TRADEMARK OFFICE
CERTIFICATE OF CORRECTION

PATENT NO. : 6,464,731 B1  
DATED : October 15, 2002  
INVENTOR(S) : Alain Genet and Alan Lagrange Page 3 of 7

It is certified that error appears in the above-identified patent and that said Letters Patent is hereby corrected as shown below:

Column 31,  
In the structure for formula (I) between lines 25-32:

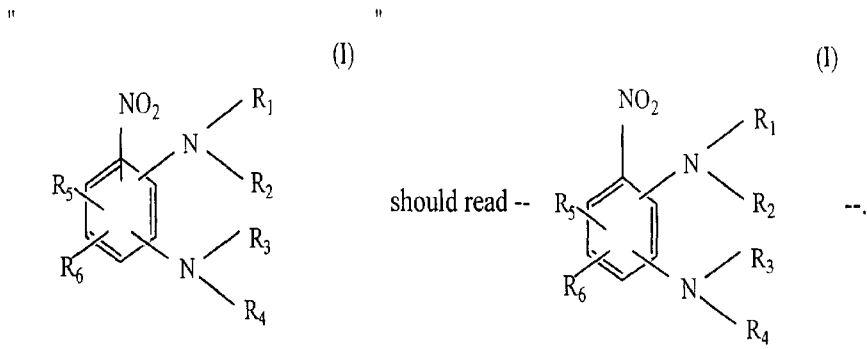

Lines 37-38, "mono-hydroxy($C_1$-$C_6$)alkyl" should read -- monohydroxy($C_1$-$C_6$)alkyl --.  
Lines 42-43, "N,N-di($C_1$-$C_6$)alkylcarbamyl($C_1C_6$)alkyl" should read  
-- N,N-di($C_1$-$C_6$)alkylcarbamyl($C_1$-$C_6$)alkyl --.  
Line 51, "radical:" should read -- radical; --.  
Line 65, "($Cl_1$-$C_6$)alkylsulphonyl," should read -- ($C_1$-$C_6$)alkylsulphonyl, --.

Column 32,  
Line 28, "polyhydroxy($C_2C_6$)alkyl" should read -- polyhydroxy($C_2$-$C_6$)alkyl --.  
Line 40, "polyhydroxy($C_1$-$C_6$)alkyl," should read -- polyhydroxy($C_2$-$C_6$)alkyl, --.  
Line 51, "a ($C_1$-$C_6$)alkyl radical;" should read -- a ($C_1$-$C_6$)alkylcarboxy($C_1$-$C_6$)alkyl radical; --.

UNITED STATES PATENT AND TRADEMARK OFFICE
CERTIFICATE OF CORRECTION

PATENT NO.   : 6,464,731 B1
DATED        : October 15, 2002
INVENTOR(S)  : Alain Genet and Alan Lagrange It is certified that error appears in the above-identified patent and that said Letters Patent is hereby corrected as shown below:

Column 33,
In the structure for formula (IV) between lines 27-32:

"
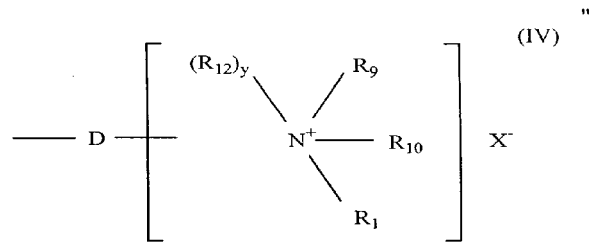
"

should read

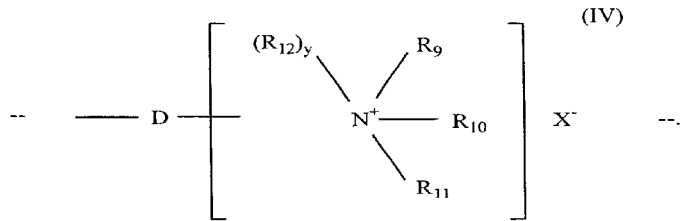
--.

Line 43, "0 to 4:" should read -- 0 to 4; --.
Line 66, "tri($C_1$-$C_{14}$)alkylsilyl($C_1$-$C_6$)alkyl" should read -- tri($C_1$-$C_6$)alkylsilyl($C_1$-$C_6$)alkyl --.

Column 35,
Line 17, "($C_1$-Ce)alkyl" should read -- ($C_1$-$C_6$)alkyl --.
Line 19, "polyhydroxy($C_1$-$C_6$)alkyl" should read -- polyhydroxy($C_2$-$C_6$)alkyl --.
Line 29, "c arded" should read -- carried --.

UNITED STATES PATENT AND TRADEMARK OFFICE
CERTIFICATE OF CORRECTION

PATENT NO. : 6,464,731 B1
DATED : October 15, 2002
INVENTOR(S) : Alain Genet and Alan Lagrange It is certified that error appears in the above-identified patent and that said Letters Patent is hereby corrected as shown below:

Column 36,
In the structure for formula (I) between lines 17-24:

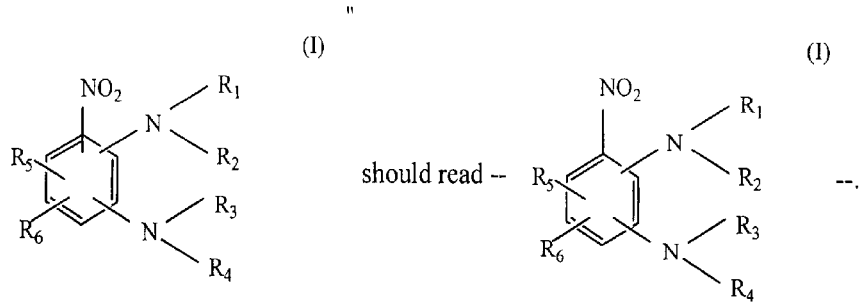

Lines 29-30, "mono-hydroxy($C_1$-$C_6$)alkyl" should read -- monohydroxy($C_1$-$C_6$)alkyl --.
Line 32, "benzyl radical:" should read -- benzyl radical; --.
Line 40, "radical:" should read -- radical; --.

Column 37,
Line 32, "polyhydroxy($C_1$-$C_6$,)alkyl," should read -- polyhydroxy($C_2$-$C_6$)alkyl, --.
Line 40, "polyhydroxy($C_1$-$C_6$)alkyl" should read -- polyhydroxy($C_2$-$C_6$)alkyl --.

UNITED STATES PATENT AND TRADEMARK OFFICE
CERTIFICATE OF CORRECTION

PATENT NO. : 6,464,731 B1
DATED : October 15, 2002
INVENTOR(S) : Alain Genet and Alan Lagrange It is certified that error appears in the above-identified patent and that said Letters Patent is hereby corrected as shown below:

<u>Column 38,</u>
In the structure for formula (IV) between lines 20-25:

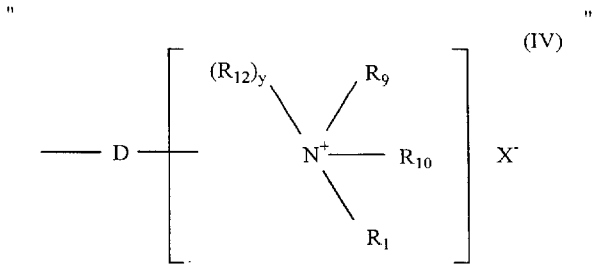

should read

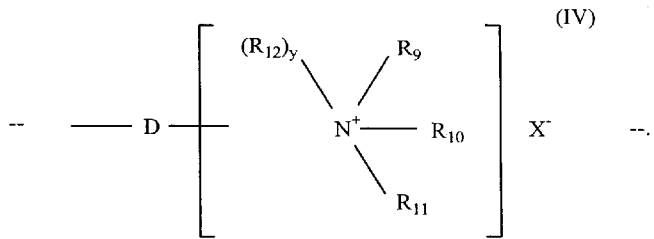

Line 55, "polyhydroxy($C_1$-$C_6$)alkyl" should read -- polyhydroxy($C_2$-$C_6$)alkyl --.

<u>Column 39,</u>
Line 39, "radical:" should read -- radical; --.
Line 47, "when x 1," should read -- when x = 1, --.

UNITED STATES PATENT AND TRADEMARK OFFICE
CERTIFICATE OF CORRECTION

PATENT NO.    : 6,464,731 B1
DATED         : October 15, 2002
INVENTOR(S)   : Alain Genet and Alan Lagrange It is certified that error appears in the above-identified patent and that said Letters Patent is hereby corrected as shown below:

Column 40,
Line 9, "nitrogen m" should read -- nitrogen atom --.

Signed and Sealed this

Fifteenth Day of April, 2003

JAMES E. ROGAN
*Director of the United States Patent and Trademark Office*